United States Patent [19]

Bozarth et al.

[11] Patent Number: 4,981,506

[45] Date of Patent: Jan. 1, 1991

[54] HERBICIDES FOR WEED CONTROL IN RICE

[75] Inventors: Gene A. Bozarth, Hockessin; Stephen K. Gee; Kanu M. Patel, both of Wilmington; Larry W. Peterson; Morris P. Rorer, both of Newark, all of Del.

[73] Assignee: E. I. DuPont de Nemours and Company, Wilmington, Del.

[21] Appl. No.: 393,902

[22] Filed: Aug. 17, 1989

Related U.S. Application Data

[63] Continuation-in-part of Ser. No. 263,102, Oct. 26, 1988, abandoned, and a continuation-in-part of Ser. No. 263,141, Oct. 26, 1988, abandoned.

[51] Int. Cl.$^5$ .................. C07D 403/12; C07D 413/12; A01N 43/54
[52] U.S. Cl. ......................................... 71/92; 544/321
[58] Field of Search ............................ 544/321; 71/92

[56] References Cited

U.S. PATENT DOCUMENTS

| | | | |
|---|---|---|---|
| 4,602,936 | 7/1986 | Topfl et al. | 71/90 |
| 4,801,327 | 1/1989 | Christensen et al. | 71/92 |
| 4,851,030 | 7/1989 | Rorer | 71/90 |

FOREIGN PATENT DOCUMENTS 164268 11/1985 European Pat. Off. .
209230 2/1987 European Pat. Off. .

OTHER PUBLICATIONS

Rorer, Chemical Abstracts, vol. 105, entry 24272c (1986).

E. I. DuPont, Chemical Abstracts, vol. 106, entry 102,328n (1987).

*Primary Examiner*—John M. Ford

[57] ABSTRACT

This invention relates to certain herbicidal sulfonamides, intermediates for their preparation, agriculturally suitable compositions of the sulfonamides and a method of use of the sulfonamides as a selective preemergent or postemergent herbicide or as a plant growth regulant.

27 Claims, No Drawings

HERBICIDES FOR WEED CONTROL IN RICE

RELATED APPLICATIONS

This is a continuation-in-part of U.S. Ser. No. 07/263,102 filed Oct. 26, 1988, now abandoned and U.S. Ser. No. 07/263,141 filed Oct. 26, 1988, now abandoned.

BACKGROUND OF THE INVENTION

This invention relates to certain herbicidal sulfonamides, agriculturally suitable compositions thereof and a method for their use as a selective Preemergent or postemergent herbicide or as a plant growth regulant, particularly for the control of undesired vegetation in rice.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, and industrial storage areas. There are many products commercially available for these purposes, but the search continues for products which are more effective, less costly and environmentally safe.

The "sulfonylurea" herbicides are an extremely potent class of herbicides discovered within the last few years which generally consist of a sulfonylurea bridge, —SO$_2$NHCONH—, linking two aromatic or heteroaromatic rings.

U.S. Pat. No. 4,801,327 and EP-A-209,230 disclose, in part, herbicidal sulfonamides of the formula

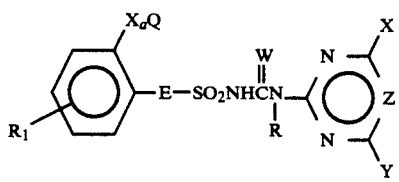

wherein $X_a$ is CH$_2$, CH(CH$_3$), CH$_2$CH$_2$, CH$_2$CH$_2$CH$_2$ or CO;

E is a single bond, CH$_2$ or O;

Q is, inter alia, a 5-membered heterocyclic ring, containing 2-4 atoms of carbon and 1-3 heteroatoms selected from the group consisting of 0-2 oxygen, wherein sulfur may take the form of S, SO or SO$_2$, and containing one or two carbonyl or sulfonyl (SO$_2$) groups, etc.; and R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CH$_2$CN, CN, CO$_2$R$_c$, C$_1$-C$_3$ haloalkyl, C$_1$-C$_3$ haloalkylthio, C$_2$-C$_4$ alkoxyalkyl, C$_2$-C$_4$ alkylthioalkyl, CH$_2$N$_3$ or NR$_d$R$_e$.

EP-A-164,268 disclose, in part, herbicidal sulfonylureas of the formula

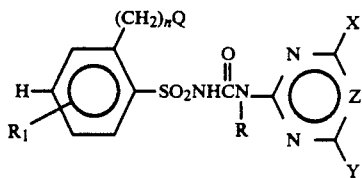

wherein

R$_1$ is H, F, Cl, Br, CH$_3$, CF$_3$, OCH$_3$, SCH$_3$, OCHF$_2$ or SCHF$_2$;

n is 1 or 2; and

Q is, inter alia, a fully unsaturated 5- or 6-membered ring containing 1 to 3 heteroatoms selected from 0-1 S, 0-1 O or 0-3 N, etc.

The compounds of the instant invention are within the generic disclosure of the above references but the compounds of the instant invention are not named and their particular utility for control of undesired vegetation in rice is not disclosed.

SUMMARY OF THE INVENTION

This invention comprises novel compounds, agriculturally suitable compositions containing them, and their method-of-use as preemergence and/or postemergence herbicides or plant growth regulants, particularly for the control of undesired vegetation in rice. The compounds of the invention are compounds of the formula

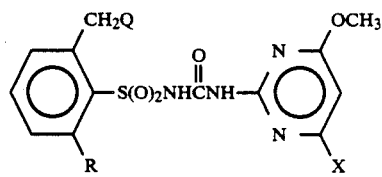

wherein

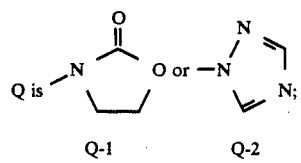

R is F, Cl, Br, CH$_3$ or SCH$_3$; and

X is CH$_3$, CH$_2$CH$_3$, OCH$_3$ or OCHF$_2$; and their agriculturally suitable salts.

Compounds of the invention preferred for reasons including ease of synthesis and/or greater herbicidal efficacy and/or greater safety to rice are:

1. Compounds of Formula I wherein R is F, Cl, Br or CH$_3$.
2. Compounds of Preferred 1 wherein R is Cl.
3. Compounds of Preferred 2 wherein X is CH$_3$ or OCH$_3$.

The compounds of the invention wherein Q is Q-1 may also be advantageously used.

Compounds of the invention specifically preferred for reasons of greatest herbicidal efficacy, greatest safety to rice, and/or most favorable ease of synthesis are 2-chloro-N-[[(4,6-dimethoxy-2-pyrimidinyl)amino]carbonyl]-6-[(2-oxo-3-oxazolidinyl)methyl]benzenesulfonamide (Formula I: Q is Q-1, R is Cl, X is OCH$_3$; m.p. 135°–136° C.);

2-chloro-N-[[(4-methoxy-6-methyl-2-pyrimidinyl-
)amino]carbonyl]-6-[(2-oxo-3-oxazolidinyl)methyl]-
benzenesulfonamide (Formula I: Q is Q-1, R is Cl, X
is CH₃; m.p. 126°-127° C.); and 2-chloro-N-[[(4,6-dimethoxy-2-pyrimidinyl)amino]car-
bonyl]]-6-[(1H-1,2,4-triazol-1-yl)methyl]benzenesul-
fonamide (Formula I: Q is Q-2, R is Cl, X is OCH₃;
m.p. 220°-221° C).

This invention also comprises novel intermediates
useful for the preparation of compounds of Formula I.
The novel intermediates include sulfonyl chlorides of
Formula II and sulfonamides of Formula III.

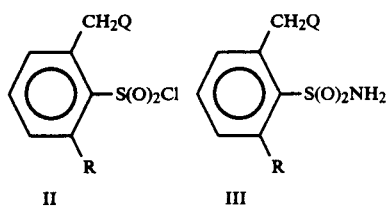

wherein

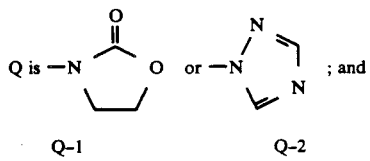

R is F, Cl, Br, CH₃ or SCH₃.

Intermediates of the present invention specifically
preferred for reasons of greatest herbicidal efficicacy,
greatest safety to rice, and/or most favorable ease of
synthesis of the derived herbicidal compounds of For-
mula I are 2-chloro-6-[(2-oxo-3-oxazolidinyl)methyl]-
benzenesulfonyl chloride (Formula II: Q is Q-1, R is Cl,
m.p. 105°-107° C.);

2-chloro-6-(1H-1,2,4-triazol-1-ylmethyl)benzenesulfo-
nyl chloride (Formula II: Q is Q-2, R is Cl); m.p.
220°-222° C.;

2-chloro-6-[(2-oxo-3-oxazolidinyl)methyl]benzenesul-
fonamide (Formula III: Q is Q-1, R is Cl; m.p.
200°-201° C.); and 2-chloro-6-(1H-1,2,4-triazol-1-ylmethyl)benzenesul-
fonamide (Formula III: Q is Q-2, R is Cl; m.p.
175°-178° C.).

The compounds of the invention are highly active
preemergent and/or postemergent herbicides or plant
growth regulants. They are especially useful for the
selective control of undesired vegetation in rice crops,
especially paddy rice. Many of the compounds of the
invention are particularly effective for control of bar-
nyardgrass. Some of the compounds also provide selec-
tive control of weeds in cereals such as wheat and bar-
ley, and in potatoes and tomatoes.

Synthesis

Compounds of Formula I can be prepared by the
procedures outlined in Equations 1 and 2.

Equation 1 illustrates a preferred method in which
sulfonamides of Formula II are reacted with 2-pyrimidi-
nyl carbamates of Formula III in the presence of an
equimolar quantity of a tertiary amine base such as
1,8-diazabicyclo[5.4.0]undec-7-ene (DBU).

Equation 1

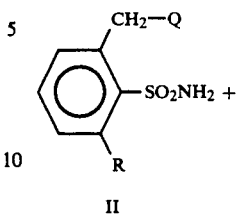

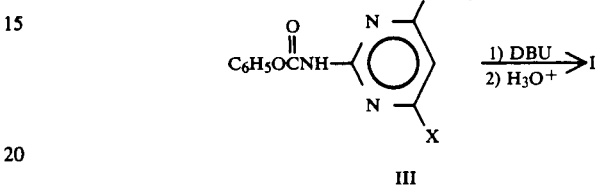

The reaction is best carried out at about −5° to 25° C.
in an inert solvent such as acetonitrile or dioxane for 0.5
to 2 hours under an inert atmosphere. The resultant
products are isolated by dilution of the reaction mixture
with water, acidification with aqueous hydrochloric
acid and filtration. Alternatively, the aqueous layer can
be extracted with a solvent such as dichloromethane or
ethyl acetate. Drying and evaporation of the solvent
affords the desired products. The phenyl carbamates III
can be prepared by treatment of the corresponding
2-aminopyrimidines with diphenyl carbonate or phenyl
chloroformate in pyridine or with sodium hydride in
dimethylformamide (DMF) at temperatures ranging
from about 20° C. to 80° C.

Alternatively, compounds of Formula I can be pre-
pared by reaction of sulfonyl carbamates of Formula IV
with the appropriate 2-aminopyrimidines of Formula V,
as illustrated in Equation 2.

Equation 2

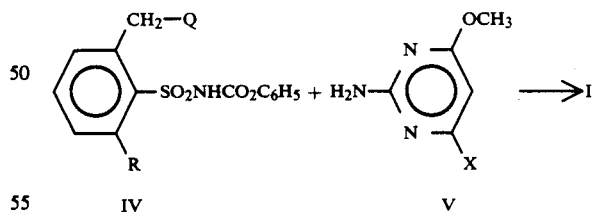

The reaction of Equation 2 is carried out at about 50°
to 100° C. in an inert solvent such as 1,4-dioxane for 0.5
to 24 hours. For further details, refer to similar reactions
in EPO Publication No. 44,807. Phenyl carbamates of
Formula IV can be prepared by methods described, or
modifications thereof, known to those skilled in the art,
e.g., U.S. Pat. No. 4,443,243.

Sulfonamides of Formula II are prepared from corre-
sponding sulfonyl chlorides VII, as illustrated in Equa-
tion 3b.

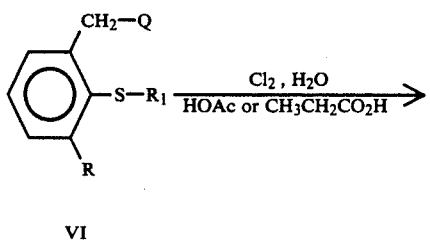

(3a)

VI

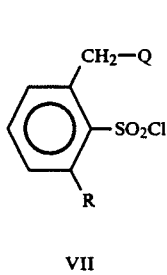

VII $$\text{VII} \xrightarrow[-40° \text{ to } 20°C.]{\text{NH}_3 \text{ or NH}_4\text{OH}} \text{II} \quad (3b)$$

wherein $R_1$ is $CH_2C_6H_5$ or $CH_2CH_2CH_3$, and R is as previously defined but not including $SCH_3$.

As shown in Equation 3b, sulfonyl chlorides VII are transformed to sulfonamides II by treatment with at least two molar equivalents of anhydrous ammonia in a solvent such as tetrahydrofuran or dichloromethane at about $-40°$ to $25°$ C. or, alternatively, with aqueous ammonium hydroxide at about $0°$ to $20°$ C.

As shown in Equation 3a, sulfonyl chlorides VII are prepared by contacting a suspension of thioether VI in a solvent such as acetic acid or propionic acid, preferably acetic acid, in the presence of at least 2.5 molar equivalents of water and at least 3.0 molar equivalents of chlorine at about $-10°$ to $30°$ C. for 0.25 to 5 hours. In some cases, particularly when acetic acid is the solvent and Q is Q-2, the products may precipitate during the reaction. In those cases, the products can be isolated and purified by filtration and washing the residue with hexane. Alternatively, hexane can be added directly to the reaction mixture to induce more precipitation, and the products are isolated by filtration. For those cases where no precipitation occurs, the reaction mixture is poured into ice-water and the product is isolated by extraction with a solvent such a dichloromethane. The extraction product is optionally washed with aqueous sodium bicarbonate until neutral or slightly basic to litmus, then dried, and the solvent is evaporated to yield a product sufficiently pure to be carried directly to step 3b.

Alternatively, oxidative chlorination of thioethers VI, wherein $R_1$ is benzyl, with a hypochlorite solution, e.g., NaOCl, can provide sulfonyl chlorides VII. For details, see analogous reactions in L. H. McKendry and N. R. Pearson, South African Patent Application No. 84/8845.

As illustrated in Equation 4, sulfonamides of Formula IIb are prepared from sulfonamides IIa, wherein $R_2$ is F, Cl or Br.

Equation 4

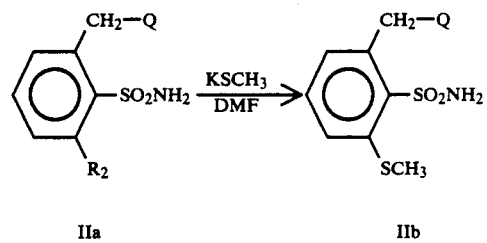

The reaction of Equation 4 is carried out using at least two molar equivalents of potassium thiomethoxide in an inert solvent such as DMF at about $80°$ to $150°$ C. for 0.5 to 8 hours. Alternatively, the N-t-butyl derivative of IIb can be prepared by reaction of the N-t-butyl derivative of IIa by conditions of Equation 4. Subsequent dealkylation with trifluoroacetic acid can then provide IIb. For details, refer to analogous reactions in J. D. Cott and W. L. Matier, *J. Org. Chem.* 39, 566 (1974).

As illustrated in Equation 5, thioethers of Formula VI, wherein R is Cl, F, Br or $CH_3$, can be prepared by the reaction of benzyl chlorides of Formula VIII with salts of heterocycles, Q.

Equation 5

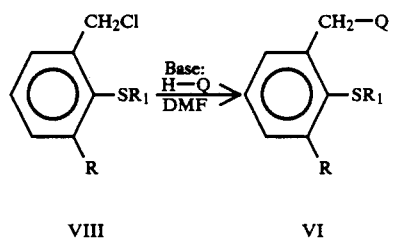

The reactions of Equation 5 can be carried out by reacting benzyl chlorides VIII with equimolar amounts of sodium or potassium salts of heterocycles, Q, in a solvent such as DMF at about $10°$ to $90°$ C. Suitable bases include sodium hydride or potassium tert-butoxide. Optionally, a phase-transfer catalyst can be used.

As illustrated in Equation 6, benzyl chlorides of Formula VIIIa can be prepared via a three step sequence from appropriately substituted benzaldehydes of Formula IX, wherein $R_2$ is F, Cl or Br.

Equation 6

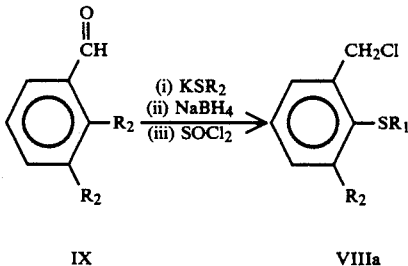

As depicted in Equation 6i, 2,3-dihalobenzaldehydes of Formula IX can be reacted with equimolar amounts of potassium benzyl mercaptan or potassium thiopropoxide in an inert solvent such as DMF at about $0°$ to 40° C. to provide the corresponding 2-halo-6-aldothioethers. After isolation and purification the thioethers can be reduced with sodium borohydride in a solvent such as ethanol by generally known conditions to provide the corresponding benzyl alcohols (Eq. 6ii). Subsequent reaction of the alcohols with excess thionyl chloride, e.g., 1 to 2 molar equivalents, in a solvent such as refluxing benzene or with equimolar amounts of thionyl chloride and a tertiary amine base such as N,N-dimethylaniline in a solvent such as chloroform at about 0° to reflux can provide benzyl chlorides of Formula VIIIa.

As illustrated in Equation 7, benzyl chlorides of Formula VIIIb can be prepared via a three-step sequence starting with 3-methyl-2-nitrobenzoic acid esters of Formula X.

Equation 7

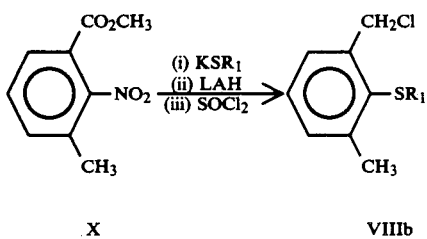

As shown in Equation 7i, 2-nitrobenzoic acid ester X can be reacted with mercaptan salts, $KSR_1$ in a solvent such as DMF at about 0° to 40° C. to provide the corresponding 2-thioether benzoic acid ester. After isolation and purification, the ester can be reduced to corresponding benzyl alcohol with reducing agents such as sodium bis(2-methoxyethoxy)aluminum hydride or lithium aluminum hydride (LAH) in a solvent such as tetrahydrofuran by generally known conditions. Subsequently, the alcohol can be reacted with thionyl chloride as described in Equation 6iii to provide benzyl chloride VIIIb.

The synthesis of heterocyclic amines such as those of Formula V has been reviewed in "The Chemistry of Heterocyclic Compounds", a series published by Interscience Publ., New York and London. Aminopyrimidines are described by D. J. Brown in "The Pyrimidines", Vol. XVI of the series mentioned above which is herein incorporated by reference. Pyrimidine of Formula V, wherein X is $OCHF_2$, can be prepared according to methods taught in U.S. Pat. No. 4,540,782.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

3-Chloro-2-[(phenylmethyl)thio]benzaldehyde

To a suspension of 112.1 g of potassium-t-butoxide in 1000 mL of dimethylformamide under a nitrogen atmosphere, 124.3 g of benzylmercaptan was added dropwise while maintaining the reaction temperature at 20°-25° C. with an ice-water bath. After stirring at 25° C. for 1.5 hours, a solution of 175 g of 2,3-dichlorobenzaldehyde dissolved in 750 mL of N,N-dimethylformamide was added dropwise, while maintaining the reaction temperature at 25°-40° with a water bath. After stirring at 25° C. for 12 hours, the reaction mixture was poured onto excess ice water to yield a precipitate. The suspension was filtered, and the isolated solid was washed with water, suction-dried and finally dried in vacuo at 40° C. overnight to afford 201 g of the title compound as a light yellow solid; m.p. 65°-68° C.

IR (Nujol) 1695 cm$^{-1}$ (C=O)

NMR (CDCl$_3$) ppm δ 10.2, (s, 1H, CHO), 7.7, (m, 2H, Ph-H), 7.35, (m, 2H, Ph-H), 7.10, (m, 2H, Ph-H), 6.90, (m, 2H, Ph-H), 4.0 (s, 2H, CH$_2$).

EXAMPLE 2

3-Chloro-2-[(phenylmethl)thio]benzenemethanol

To a suspension of 54 9 of the compound of Example 1 in 500 mL of ethanol, 7.8 g sodium borohydride was added portionwise, while maintaining the reaction temperature at 25-35° C. with an ice-water bath. The mixture was stirred at 25° C. for 2 hours. The ethanol was removed by rotary evaporator, and the residue was suspended in 500 mL water and extracted with methylene chloride. The organic layer was washed with water, dried over magnesium sulfate, filtered and the filtrate evaporated to leave the title compound as a yellow solid; m.p. 45°-47° C.

IR (Nujol) 3300 cm$^{-1}$ (OH)

NMR (CDCl$_3$) ppm δ 7.3, (m, 8H, Ph-H), 4.4, (s, 2H, CH$_2$), 4.0, (s, 2H, CH$_2$O), 1.8, (bs 1H, OH).

EXAMPLE 3

1-Chloro-3-(chloromethyl)-2-[(phenylmethyl)thio]benzene

To a mixture of 54 g of the compound of Example 2 in 200 mL of chloroform (ethanol-free) and of N,N-dimethylaniline, a solution of 30 g of thionyl chloride in 50 mL of chloroform (ethanol-free) was added while maintaining the reaction temperature at 15° C. with an ice-water bath. The mixture was stirred at 25° C. for 1 hour, then refluxed for 3 hours. The mixture was acidified with 1 N aqueous hydrochloric acid and the organic layer was collected. The organic layer was washed once with 1 N aqueous hydrochloric acid, dried over magnesium sulfate, and filtered. The filtrate was passed through a silica gel column, eluted with methylene chloride, and after evaporation of the eluant, 54 g subject compound was obtained as a yellow oil.

IR (Neat) 3010 cm$^{-1}$ (OH)

NMR (CDC$_{13}$): ppm δ 7.3, (m, 8H, Ph-H), 4.5, (s, 2H, CH$_2$), 4.1, (s, 2H, CH$_2$).

EXAMPLE 4

1-[[3-Chloro-2-[(phenylmettyl)thio]phenyl]methyl]-1H-1,2,4-triazole

To a suspension of 2.5 g of the sodium salt of 1,2,4-triazole in 30 mL of dimethylfornamide, containing 2.22 g of benzyltriethylammonium chloride (a phase transfer catalyst), 7.1 g of the product of Example 3 was added in one Portion. The mixture was stirred at 25° C. for 24 hours, poured into 100 mL water and extracted with ethyl acetate. The organic layer was dried over magnesium sulfate, filtered and the filtrate was evaporated to yield a crude yellow oil. Silica gel column chromatography, eluting with ethyl acetate, after evaporation afforded the subject compound as a yellow oil.

NMR (CDCl$_3$) ppm δ 7.9, (s, 1H, triazole-H), 7.81, (s, 1H, triazole-H), 7.50, (d of d, 1H, Ar-H), 7.35, (m, 5H, Ar-H), 7.10, (m, 1H, Ar-H), 6.31, (d of d, 1H, Ar-H), 5.10, (s, 2H, CH$_2$), 4.00, (s, 2H, CH$_2$).

EXAMPLE 5

2-Chloro-6-(1H-1,2,4-triazol-1-ylmethyl)benzenesulfonamide

To a solution of 4.5 g of the compound of Example 4 dissolved in 100 mL of acetic acid, containing 0.7 mL of water, and cooled to 15° C., was added 6.5 mL of condensed chlorine. A slight exotherm of 5° C. was noted. The reaction was stirred for 45 minutes, and the resulting sulfonyl chloride solid was collected by filtration and washed with hexane. The solid was immediately dissolved in 50 mL of tetrahydrofuran, cooled to 15° C. and treated with 5 mL of concentrated ammonium hydroxide and stirred for 1 hours. The tetrahydrofuran was removed on a rotary-evaporator to yield a residue which was suspended in water and in diethyl ether and filtered to afford 2.72 g of the title compound as a white solid; m.p. 175°-178° C.

IR (KBr): 3400 and 3210 cm$^{-1}$ SO$_2$NH$_2$

NMR (DMSO-d$_6$) ppm δ 8.60, (s, 1H, triazole-H), 8.00, (s, 1H, triazole-H), 7.61, (d, 1H, Ph-H), 7.42, (m, 1H, Ph-H), 7.39, (s, 2H, SO$_2$NH$_2$), 6.70, (m, 1H, Ph-H), 5.90, (s, 2H, CH$_2$).

EXAMPLE 6

2-Chloro-N-[[(4,6-dimethoxy-2-pyrimidinyl)amino]carbonyl]-6-[(1H-1,2,4-triazol-1-yl)methyl]benzenesulfonamide To a suspension of 0.14 g of the product of Example 5 in 5 mL of acetonitrile, containing 0.17 g of phenyl (4,6-dimethoxypyrimidin-2-yl)carbamate, was added 0.10 mL of 1,8-diazabicyclo[5.4.0]undec-7-ene (DBU). The resultant solution was stirred at 25° C. for 2 hours, diluted with 10 mL of cold water and acidified with 5 mL 5% aqueous hydrochloric acid. The resulting solid was filtered. The collected white solid was washed with water, diethyl ether and suction-dried and finally dried in vacuo overnight to afford 0.17 g of the title compound as a white solid; m.p. 220°-221° C.

NMR (DMSO-d$_6$) ppm δ 13.15, (bs, 1H, NH), 10.85, (bs, 1H, NH), 8.64, (s, 1H, triazole-H), 8.0, (s, 1H, triazole-H), 7.70, (m, 2H, Ph-H), 6.75, (m, 1H, Ph-H), 6.021, (m, 3H, CH$_2$ & Py-H), 3.91; (s, 6H, OCH$_3$).

EXAMPLE 7

3-[[3-Chloro-2-[(phenylmethyl)thio]phenyl]methyl]-2-oxazolidinone

To a Suspension of 0.9 g sodium hydride (hexane washed) in 15 mL of N,N-dimethylformamide, a solution of 3.05 g of 2-oxazolidone in 15 mL of N,N-dimethylformamide was added at room temperature. As a white precipitate formed, the mixture was heated slowly to 80° C. over 30 minutes and kept at 80° C. for another 30 minutes. The mixture was cooled to room temperature, and a solution of 8.5 g of the compound of Example 3 in 20 mL of N,N-dimethylformamide was added in one portion. The resulting solution was stirred at 25° C. for 12 hours, poured into 50 mL water and extracted with ethyl acetate. The organic layer was washed well with water, dried over magnesium sulfate, filtered, and the filtrate evaporated to leave a yellow oil. Silica gel flash chromatography (4:1 hexane-ethyl acetate eluant) afforded after evaporation of the eluant 7.5 g of the subject compound as a yellow oil.

NMR (CDCl$_3$) ppm δ 7.7, (d, 1H, Ar-H), 7.2, (m, 5H, Ar-H), 7.0, (m, 2H, Ar-H), 4.3, (s, 2H, CH$_2$), 4.25, (t, 2H, CH$_2$), 4.0, (s, 2H, CH$_2$), 3.1, (t, 2H, CH$_2$).

EXAMPLE 8

2-Chloro-6-[(2-oxo-3-oxazolidinyl)methyl]benzenesulfonamide

To a solution of 7.5 g of the compound of Example 7 dissolved in 100 ml of acetic acid, containing 1.0 ml of water and cooled to 15° C., was added 8.8 mL of condensed chlorine. A slight exotherm of 5° C. was noted. The reaction was stirred for an additional 30 minutes, poured into ice-cold water, and extracted with methylene chloride. The organic layer was washed with saturated aqueous sodium bicarbonate solution, dried over magnesium sulfate, filtered, and evaporated to provide the intermediate sulfonyl chloride as an oil. The oil was immediately dissolved in 100 mL of tetrahydrofuran, cooled to 15° C. and treated with 6 mL of concentrated ammonium hydroxide and stirred for 1 hour. The tetrahydrofuran was removed on a rotary evaporator to yield a residue which was suspended in water and diethyl ether and filtered to provide 5.0 g of the title compound as an off-white solid; m.p. 200°-201° C.

IR (KBr): 1745 cm$^{-1}$ (C=O)

In a similar reaction the intermediate sulfonyl chloride was isolated as a solid by slurrying the crude sulfonyl chloride oil in 1-chlorobutane and filtration; m.p. 105°-107° C.

EXAMPLE 9

2-Chloro-N-[[(4,6-dimethoxy-2-pyrimidinyl)amino]carbonyl]-6-[(2-oxo-3-oxazolidinyl)methyl]benzenesulfonamide To a suspension of 0.15 g of the product of Example 8 in 5 mL of acetonitrile, containing 0.15 g of phenyl (4,6-dimethoxypyrimidin-2-yl)carbamate, was added 0.15 mL of 1,8-diazabicyclo[5.4.0]undec-7-ene (DBU). The resultant solution was stirred at 25° C. for 2 hours, diluted with 10 mL of cold water and acidified with 5 mL of 5% aqueous hydrochloric acid. The resulting precipitate was filtered. The collected white solid was washed with water, diethyl ether and suction-dried and finally dried in vacuo overnight to afford 0.14 g of the title compound as a white solid; m.p. 135°-136° C. When the solid was dried in methylene chloride over magnesium sulfate and the solvent removed under reduced pressure, the title compound, as a white solid, now had m.p. 227°-229° C. Spectra (IR and NMR) for both solids appeared identical.

IR (KBr): 1740 (C=O); 1710 (C=O) cm$^{-1}$

NMR (CDCl$_3$) ppm δ 12.95, (bs, 1H, NH), 7.58, (m, 1H, Ar-H), 7.50, (m, 2H, Ar-H), 7.18, (bs, 1H, NH), 5.80, (s, 1H, PyH), 5.20, (s, 2H, CH$_2$), 4.38, (t, 2H, CH$_2$), 3.96, (s, 6H, OCH$_3$), 3.67, (t, 2H, CH$_2$).

EXAMPLE 10

2-Chloro-N-[[(4-methoxy-6-methyl-2-pyrimidinyl)amino]carbonyl]-6-[(2-oxo-3-oxazolidinyl)methyl]benzenesulfonamide By the procedure of Example 9, 0.15 g of the product of Example 8 was reacted with 0.15 g of phenyl (4-methyl-6-methoxypyrimidin-2-yl)carbamate and 0.15 mL of 1,8-diazabicyclo[5.4.0]undec-7-ene (DBU) in 5 mL of acetonitrile. The isolated crude solid was purified by slurry-washing with 20 mL of diethyl ether to yield 0.13 g of the subject compound; m.p. 126°-127° C.

IR (KBr): 1730 (C=O) 1710 (C=O) cm$^{-1}$

NMR (CDCl$_3$) ppm δ 13.50; (bs, 1H, NH), 7.55, (m, 1H, Ar-H), 7.51, (m, 2H, Ar-H), 7.20, (bs, 1H, NH), 6.31, (s, 1H, Py-H), 5.21, (s, 2H, CH$_2$), 4.37, (t, 2H, CH$_2$), 3.94, (s, 3H, OCH$_3$), 3.69, (t, 2H, CH$_2$), 2.43 (s, 3H, CH$_3$).

Using the techniques described in Equations 1–7 and Examples 5 and 8, or simple modifications thereof, the following sulfonyl chlorides and sulfonamides in Tables 1 and 2, respectively, can be made by one skilled in the art.

TABLE 1

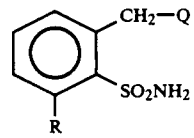

| Q | R | m.p. |
|---|---|---|
| Q-1 | Cl | 105–107° |
| Q-1 | F | oil |
| Q-1 | Br | |
| Q-1 | CH$_3$ | oil |
| Q-1 | SCH$_3$ | |
| Q-2 | Cl | 220–222° |
| Q-2 | F | 193–197° |
| Q-2 | Br | |
| Q-2 | CH$_3$ | oil |
| Q-2 | SCH$_3$ | |

TABLE 2

| Q | R | m.p. |
|---|---|---|
| Q-1 | F | 224–228° |
| Q-1 | Cl | 200–201° |
| Q-1 | Br | |
| Q-1 | CH$_3$ | 203–209° |
| Q-1 | SCH$_3$ | |
| Q-2 | F | 158–161° |
| Q-2 | Cl | 175–178° |
| Q-2 | Br | |
| Q-2 | CH$_3$ | 162–163° |
| Q-2 | SCH$_3$ | |

Using the techniques described in Equations 1–7 and Examples 6, 9 and 10, or simple modifications thereof, the following compounds in Table 3 can be made by one skilled in the art.

TABLE 3

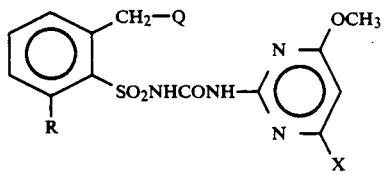

| Q | R | X |
|---|---|---|
| Q-1 | Cl | OCH$_3$ |
| Q-1 | Cl | OCHF$_2$ |
| Q-1 | Cl | CH$_3$ |
| Q-1 | Cl | CH$_2$CH$_3$ |
| Q-1 | F | OCH$_3$ |
| Q-1 | F | OCHF$_2$ |
| Q-1 | F | CH$_3$ |
| Q-1 | F | CH$_2$CH$_3$ |
| Q-1 | Br | OCH$_3$ |
| Q-1 | Br | OCHF$_2$ |
| Q-1 | Br | CH$_3$ |
| Q-1 | Br | CH$_2$CH$_3$ |
| Q-1 | CH$_3$ | OCH$_3$ |
| Q-1 | CH$_3$ | OCHF$_2$ |
| Q-1 | CH$_3$ | CH$_3$ |
| Q-1 | CH$_3$ | CH$_2$CH$_3$ |
| Q-1 | SCH$_3$ | OCH$_3$ |
| Q-1 | SCH$_3$ | OCHF$_2$ |
| Q-1 | SCH$_3$ | CH$_3$ |
| Q-1 | SCH$_3$ | CH$_2$CH$_3$ |
| Q-2 | Cl | OCH$_3$ |
| Q-2 | Cl | OCHF$_2$ |
| Q-2 | Cl | CH$_3$ |
| Q-2 | Cl | CH$_2$CH$_3$ |
| Q-2 | F | OCH$_3$ |
| Q-2 | F | OCHF$_2$ |
| Q-2 | F | CH$_3$ |
| Q-2 | F | CH$_2$CH$_3$ |
| Q-2 | Br | OCH$_3$ |
| Q-2 | Br | OCHF$_2$ |
| Q-2 | Br | CH$_3$ |
| Q-2 | Br | CH$_2$CH$_3$ |
| Q-2 | CH$_3$ | OCH$_3$ |
| Q-2 | CH$_3$ | OCHF$_2$ |
| Q-2 | CH$_3$ | CH$_3$ |
| Q-2 | CH$_3$ | CH$_2$CH$_3$ |
| Q-2 | SCH$_3$ | OCH$_3$ |
| Q-2 | SCH$_3$ | OCHF$_2$ |
| Q-2 | SCH$_3$ | CH$_3$ |
| Q-2 | SCH$_3$ | CH$_2$CH$_3$ |

Formulations

Useful formations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 2

| | Active Ingredient | Weight Percent* Diluent(s) | Surfactant(s) |
|---|---|---|---|
| Wettable Powder | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 11

| Wettable Powder | |
|---|---|
| 2-chloro-N-[[(4,6-dimethoxy-2-pyrimidinyl)-amino]carbonyl]-6-[(2-oxo-3-oxazolidinyl)-methyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 50 microns in diameter. The product is reblended before packaging.

EXAMPLE 12

| Granule | |
|---|---|
| Wettable Powder of Example 11 | 5% |
| attapulgite granules | 95% |
| (U.S.S. 20–40 mesh; 0.84–0.42 mm) | |

A slurry of wettable powder containing 25% solids is sprayed on the surface of attapulgite granules in a double-cone blender. The granules are dried and packaged.

EXAMPLE 13

| Extruded Pellet | |
|---|---|
| 2-chloro-N-[[(4-methoxy-6-methyl-2-pyrimidinyl)amino]caronyl]-6-[(2-oxo-3-oxazolidinyl)methyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

| Low Strength Granule | |
|---|---|
| 2-chloro-N-[[(4,6-dimethoxy-2-pyrimidinyl)-amino]carbonyl]-6-[(2-oxo-3-oxazolidinyl)-methyl]benzenesulfonamide | 1% |
| N,N-dimethylformamide | 9% |
| attapulgite granules | 90% |
| (U.S.S. 20–40 sieve, 0.42 to 0.84 mm) | |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| 2-chloro-N-[[(4-methoxy-6-methyl-2-pyrimidin-yl)amino]carbonyl]-6-[(2-oxo-3-oxazolidin-yl)methyl]benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Oil Suspension | |
|---|---|
| 2-chloro-N-[[(4,6-dimethoxy-2-pyrimidinyl)-amino]carbonyl]-6-[(2-oxo-3-oxazolidinyl)-methyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 17

| Granule | |
|---|---|
| 2-chloro-N-[[(4-methoxy-6-methyl-2-pyrimidin-yl)amino]carbonyl]-6-[(2-oxo-3-oxazolidin-yl)methyl]benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh (149 microns) screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 18

| High Strength Concentrate | |
|---|---|
| 2-chloro-N-[[(4,6-dimethoxy-2-pyrimidinyl)-amino]carbonyl]-6-[(2-oxo-3-oxazolidinyl)-methyl]benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| 2-chloro-N-[[(4-methoxy-6-methyl-2-pyrimidin-yl)amino]carbonyl]-6-[(2-oxo-3-oxazolidin-yl)methyl]benzenesulfonamide | 90% |
| dioctyl sodium sulfosuccinate | 0.1% |
| synthetic fine silica | 9.9% |

The ingredients are blended and ground in a hammer-mill to produce particles essentially all below microns. The material is sifted through a U.S.S. No. 50 screen and then packaged.

EXAMPLE 20

| Wettable Powder | |
|---|---|
| 2-chloro-N-[[(4,6-dimethoxy-2-pyrimidinyl)-amino]carbonyl]-6-[(2-oxo-3-oxazolidinyl)-methyl]benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Dust | |
|---|---|
| 2-chloro-N-[[(4-methoxy-6-methyl-2-pyrimidin-yl)amino]carbonyl]-6-[(2-oxo-3-oxazolidin-yl)methyl]benzenesulfonamide | 10% |
| attapulgite | 10% |
| talc | 80% |

The active ingredient is blended with attapulgite and then passed through a hammer-mill to produce particles substantially all below 200 microns. The ground concentrate is then blended with powdered pyrophyllite until homogeneous.

EXAMPLE 22

| Solution | |
|---|---|
| 2-chloro-N-[[(4-methoxy-6-methyl-2-pyrimidin-yl)amino]carbonyl]-6-[(2-oxo-3-oxazolidin-yl)methyl]benzenesulfonamide, sodium salt | 5% |
| water | 95% |

The salt is added directly to the water with stirring to produce the solution, which may then be packaged for use.

EXAMPLE 23

| Solution | |
|---|---|
| 2-chloro-N-[[(4,6-dimethoxy-2-pyrimidin-yl)amino]carbonyl]-6-[(2-oxo-3-oxazolidin-yl)methyl]benzenesulfonamide, sodium salt | 5% |
| water | 95% |

The salt is added directly to the water with stirring to produce the solution, which may then be packaged for use.

EXAMPLE 24

| Wettable Powder | |
|---|---|
| 2-chloro-N-[[(4,6-dimethoxy-2-pyrimidinyl)-amino]carbonyl]-6-[(1H-1,2,4-triazol-1-yl)-methyl]benzenesulfonamide, | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 50 microns in diameter. The product is reblended before packaging.

EXAMPLE 25

| Granule | |
|---|---|
| Wettable Powder of Example 24 | 5% |
| attapulgite granules (U.S.S. 20–40 mesh; 0.84–0.42 mm) | 95% |

A slurry of wettable powder containing 25% solids is sprayed on the surface of attaplugite granules in a double-cone blender. The granules are dried and packaged.

UTILITY

Test results indicate that compounds of the present invention are highly active preemergent and/or postemergent herbicides or plant growth regulants. These compounds have utility for selected grass, sedge and broadleaf weed control in dry-land and paddy rice. Many of the compounds of this invention are particularly useful for the control of barnyardgrass and selected broadleaf weeds in paddy rice. Several compounds of this invention are useful for grass and broadleaf weed control in cereal crops such as barley, oats, triticale, and wheat, and in potatoes and tomatoes. Several compounds are especially useful for control of barnyardgrass and selected broadleaf weeds and sedges such as waterchestnut and water plantain in transplanted paddy rice. These compounds also have utility for broad-spectrum pre- and/or postemergence weed control in areas where complete control of all vegetation is desired such as around storage tanks, parking lots, drive-in theaters, billboards, highways, railroad structures, and in fallow areas. Alternatively, these compounds are useful to modify plant growth or as citrus abscission agents.

Rates of application for compounds of this invention are determined by a number of factors. These factors include: formulation selected, method of application, amount of vegetation present, growing conditions, etc. In general terms, the subject compounds should be applied at rates from 0.0005 to 20 kg/ha, with a preferred rate range of from 0.001 to 0.25 kg/ha. Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| anilofos | S-4-chloro-N-isopropylcarbaniloyl-methyl-O,O-dimethyl phosphorodithioate |
| bensulfuron methyl | 2-[[[[[(4,6-dimethoxy-2-pyrimidinyl)amino]sulfonyl]methyl]-benzoic acid, methyl ester |
| benfuresate | 2,3-dihydro-3,3-dimethylbenzofuran-5-yl)ethanesulphonate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| bifenox | methyl 5-(2,4-dichlorophenoxy)-2-nitrobenzoate |
| bromoxynil | 3,5-dibromo-4-hydroxybenzonitrile |
| butachlor | N-(butoxymethyl)-2-chloro-N-(2,6-diethylphenyl)acetamide |
| chlormethoxynil | 2,4-dichlorophenyl 4-nitro-3-methoxyphenyl ether |
| chlornitrofen | 2,4,6-trichlorophenyl-4-nitrophenyl ether |
| cinmethylin | exo-1-methyl-4-(1-methylethyl)-2-[(2-methylphenyl)methoxy]-7-oxa-bicyclo[2.2.1]heptane |
| CGA 142'464 | 3-(4,6-dimethoxy-1,3,5-triazin-2-yl)-1-[2-(2-methoxyethoxy)-phenylsulfonyl]-urea |
| desmetryn | 2-(isopropylamino)-4-(methylamino)-6-(methylthio)-s-triazine |
| dichlobenil | 2,6-dichlorobenzonitrile |
| dimepiperate | S-1-methyl-1-phenylethylpiperidine-1-carbothioate |
| dymron | N-(4-methylphenyl)-N'-(1-methyl-1-phenylethyl)urea |
| esprocarb (SC2957) | S-benzyl-N-ethyl-N-(1,2-dimethylpropyl)thiolcarbamate |
| ethofumesate | (±)-2-ethoxy-2,3-dihydro-3,3-dimethyl-5-benzofuranyl methanesulfonate |
| fenoxaprop | (±)-2-[4-[(6-chloro-2-benzoxazolyl)-oxy]phenoxy]propanoic acid |
| fluazifop | (±)-2-[4-[[5-(trifluoromethyl)-2-pyridinyl]oxy]phenoxy]propanoic acid |
| fluorodifen | p-nitrophenyl α,α,α-trifluoro-2-nitro-p-tolyl ether |
| fomesafen | 5-[2-chloro-4-(trifluoromethyl)-phenoxy]-N-(methylsulfonyl)-2-nitrobenzamide |
| lactofen | (±)-2-ethoxy-1-methyl-2-oxoethyl-5-[2-chloro-4-(trifluoromethyl)-phenoxy]-2-nitrobenzoate |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothioate |
| mefluidide | N-[2,4-dimethyl-5-[[(trifluoromethyl)sulfonyl]amino]phenyl]-acetamide |
| mefenacet | 2-(2-benzothiazolyloxy-N-methyl-N-phenylacetamide |
| methazole | 2-(3,4-dichlorophenyl)-4-methyl-1,2,4-oxadiazolidine-3,5-dione |
| metsulfuron methyl | 2-[[[[(4-methoxy-6-methyl-1,3,5-tri-azin-2-yl)amino]carbonyl]-amino]sulfonyl]benzoic acid, methyl ester |
| molinate | S-ethyl hexahydro-1H-azepine-1-carbothioate |
| monuron | N'-(4-chlorophenyl)-N,N-dimethylurea |
| nitrofen | 2,4-dichloro-1-(4-nitrophenoxy)-benzene |
| norflurazon | 4-chloro-5-(methylamino)-2-[3-(trifluoromethyl)phenyl]-3(2H)-pyridazinone |
| oryzalin | 4-(dipropylamino)-3,5-dinitrobenzene-sulfonamide |

-continued

| Common Name | Chemical Name |
|---|---|
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| pendimethalin | N-(1-ethylpropyl)-3,4-dimethyl-2,6-dinitrobenzenamine |
| pretilachlor | α-chloro-2,6-diethyl-N-(2-propoxyethyl)-acetanilide |
| propanil | N-(3,4-dichlorophenyl)propanamide |
| pyrazosulfuron ethyl | ethyl 5-[3-(4,6-dimethoxypyrimidin-2-yl)ureadosulfonyl]-1-methylpyrazole-4-carboxylate |
| pyrazolate | 4-(2,4-dichlorobenzoyl)-1,3-dimethyl-pyrazol-5-yl-p-toluenesulphonate |
| quizalofop ethyl | (±)-2-[4-[(6-chloro-2-quinoxalinyl)oxy]phenoxy]propanoic acid, ethyl ester |
| quinclorac | 3,7-dichloro-8-quinoline carboxylic acid |
| SK-233 | 1-(α,α-dimethylbenzyl)-3-(4-methylphenyl)urea |
| thiobencarb | S-[(4-chlorophenyl)methyl] diethylcarbamothioate |
| triclopyr | [(3,5,6-trichloro-2-pyridinyl)oxy]acetic acid |
| 2,4-D | (2,4-dichlorophenoxy)acetic acid |
| 2,4-DB | 4-(2,4-dichlorophenoxy)butanoic acid |
| — | 1-(α,α-dimethylbenzyl)-3-p-toluylurea |
| — | 1-α,α-dimethyl-p-methylbenzyl-3-p′-toluylurea |

Herbicidal properties of the subject compounds were discovered in a number of greenhouse tests. Test procedures and results follow.

Compounds

[Structure diagram showing a benzene ring with CH$_2$Q and R substituents connected via S(O)$_2$NHCNH(=O) linker to a pyridine ring with OCH$_3$ and X substituents]

Q is —N(C=O)(CH$_2$CH$_2$)— (Q-1) or —N—N=CH—N= (triazole, Q-2)

| Compound # | Q | R | X | m.p. (°C.) |
|---|---|---|---|---|
| 1 | Q-1 | Cl | OCH$_3$ | 135–136 |
| 2 | Q-1 | Cl | CH$_3$ | 126–127 |
| 3 | Q-1 | F | OCH$_3$ | 200–205 |
| 4 | Q-1 | F | CH$_3$ | 127–128 |
| 5 | Q-1 | CH$_3$ | OCH$_3$ | 135–138 |

Compounds

[Same structure as above]

| Compound # | Q | R | X | m.p. (°C.) |
|---|---|---|---|---|
| 6 | Q-1 | CH$_3$ | CH$_3$ | 141–145 |
| 7 | Q-1 | Cl | OCF$_2$H | 200–204 |
| 8 | Q-1 | Cl | CH$_2$CH$_3$ | 131–133 |
| 9 | Q-2 | Cl | OCH$_3$ | 220–221 |
| 10 | Q-2 | Cl | CH$_3$ | 198–199 |
| 11 | Q-2 | F | OCH$_3$ | 195–200 |
| 12 | Q-2 | F | CH$_3$ | 193–198 |
| 13 | Q-2 | CH$_3$ | OCH$_3$ | 240–241 |
| 14 | Q-2 | CH$_3$ | CH$_3$ | 214–217 |

Seeds of barley (*Hordeum volgare*), barnyardgrass (*Echinochloa crus-galli*), cheatgrass (*Bromus secalinus*) or downy brome (*Bromus tectorum*), cocklebur (*Xanthium pensylvanicum*), corn (*Zea mays*), cotton (*Gossypium hirsutum*), crabgrass (*Digitaria* spp.), giant foxtail (*Setaria faberi*), morningglory (*Ipomoea* spp.), rice (*Oryza sativa*), sorghum (*Sorghum bicolor*), soybean (*Glycine max*), sugar beet (Beta vulcaris), velvetleaf (*Abutilon theophrasti*) wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. The ratings, summmarized in Table A, are based on a scale of 0 to 10 where 0 is no effect and 10 is complete control. A dash (-) response means no test result. The accompanying descriptive symbols have the following meanings:

C = chlorosis/necrosis;
G = growth retardation;
H = formative effect; and
U = unusual pigmentation.

TABLE A

| | Cmpd 1 | | Cmpd 2 | | Cmpd 3 | | Cmpd 4 | |
|---|---|---|---|---|---|---|---|---|
| Rate (g/ha) | 50 | 10 | 50 | 10 | 50 | 10 | 50 | 10 |
| POSTEMERGENCE | | | | | | | | |
| Barley | 3C,6G | 2C,5G | 2C,5G | 2C,5G | 2C,6G | 2G | 3C,8G | 0 |
| Barnyardgrass | 10C | 9C | 9C | 9C | 9C | 9C | 9C | 3C,9H |
| Cheatgrass | — | — | — | — | 8G | 5G | 8G | 5G |
| Cocklebur | 9C | 9C | 9C | 10C | 10C | 10C | 10C | 9C |
| Corn | 10C | 5C,9G | 10C | 4C,9G | 9C | 4U,9G | 3C,9G | 2C,9G |
| Cotton | 10C | 9C | 10C | 9C | 9C | 4C,9G | 9C | 4C,9G |
| Crabgrass | 9C | 4C,9G | 3C,7G | 5G | 2C,7G | 2G | 4C,9H | 3C,7G |
| Downy brome | 10C | 9C | 3C,7G | 2C,7G | — | — | — | — |
| Giant foxtail | 9C | 4C,7G | 4C,9H | 2C,6G | 2C,9G | 7G | 4C,7G | 3C,7G |

TABLE A-continued

| | | | | | | | | |
|---|---|---|---|---|---|---|---|---|
| Morningglory | 10C | 10C | 10C | 10C | 9C | 4C,9G | 10C | 4C,9G |
| Nutsedge | 10C | 4C,9G | — | 0 | 5G | 2C,2G | 2G | 0 |
| Rice | 4C,9G | 2C,5G | 2C,9G | 6G | 3C,8G | 5G | 3C,8G | 2C,4G |
| Sorghum | 10C | 9C | 9C | 5C,9G | 4C,9G | — | 5C,9G | 5C,9G |
| Soybean | 9C | 9C | 9C | 5C,9G | 3C,9G | 3C,8H | 4C,9G | 3C,7H |
| Sugar beet | 10C | 9C | 10C | 10C | 9C | 9C | 9C | 9C |
| Velvetleaf | 9C | 9C | 10C | 9C | 10C | 5C,9G | 9C | 4C,9H |
| Wheat | 3C,7G | 4G | 3C,6G | 4G | 3G | 0 | 6G | 0 |
| Wild oat | 3C,7G | 3G | 2C,5G | 3C,3G | 4G | 0 | 2C,4G | 0 |
| PREEMERGENCE | | | | | | | | |
| Barley | 0 | 0 | 3C,5G | 2C,3G | 8G | 3G | 2C,5G | 2C |
| Barnyardgrass | 9H | 8H | 9H | 3C,8H | 9H | 8H | 9H | 3C,7H |
| Cheatgrass | — | — | — | — | 9G | 3G | 8G | 7G |
| Cocklebur | 8H | 3H | 9H | 6H | 9H | 3C,7H | 8H | 2C,3G |
| Corn | 3C,9G | 9G | 5C,9G | 2C,4G | 3C,9G | 2C,8H | 3C,9H | 3C,8G |
| Cotton | 2C,5G | 0 | 3C,6G | 2G | 9G | 9G | 3C,9G | 2C,7H |
| Crabgrass | 3C,6G | 3C,5G | 3C,6G | 2C,2G | 9H | 5G | 9H | 3C,7G |
| Downy brome | 9H | 8H | 9H | 3C,8H | — | — | — | — |
| Giant foxtail | 6G | 3G | 9H | 2C,2G | 9H | 5G | 8H | 3C,6G |
| Morningglory | 9G | 8H | 9G | 7H | 9G | 9G | 3C,9H | 7H |
| Nutsedge | 9G | 0 | 7G | 0 | 5G | 0 | 3G | 0 |
| Rice | 7G | 2G | 3C,6G | 2C,4G | 9H | 7G | 2C,8G | 2C,5G |
| Sorghum | 10H | 9H | 9H | 3C,8G | 3C,9H | 8G | 3C,9H | 3C,8H |
| Soybean | 8H | 3C,5H | 9H | 3C,7G | 3C,8H | 6G | 3C,7H | 3C,4H |
| Sugar beet | 5C,9G | 9G | 5C,9G | 5C,9G | 4C,9G | 4G | 4C,9G | 4C,9G |
| Velvetleaf | 9H | 7H | 5C,9H | 6H | 8H | 3H | 3C,7H | 2C,4H |
| Wheat | 2G | 0 | 8G | 2G | 4G | 0 | 5G | 0 |
| Wild oat | 2G | 2G | 6G | 2G | 2C,5G | 2G | 2C,5G | 2C,2G |

| | Cmpd 5 | | Cmpd 6 | | Cmpd 7 | | Cmpd 8 | |
|---|---|---|---|---|---|---|---|---|
| RATE (g/ha) | 50 | 10 | 50 | 10 | 50 | 10 | 50 | 10 |
| POSTEMERGENCE | | | | | | | | |
| Barley | 5G | 0 | 3C,5G | 1C | 2G | 0 | 2C,2G | 0 |
| Barnyardgrass | 9C | 3C,9H | 9C | 5C,9G | 3C,7H | 3C,7G | 5C,9H | 2C,6H |
| Cheatgrass | 9G | 2C,7G | 2C,7G | 2C,3G | 2C,9G | 2C,8G | 9G | 8G |
| Cocklebur | 4C,9G | 9C | 9C | 4C,9G | 4C,9G | 3C,7H | 5C,9G | 3C,7G |
| Corn | 3C,9G | 2C,5G | 2C,9G | 3C,6G | 3C,8G | 3C,7H | 3C,8G | 2C,4G |
| Cotton | 9C | 10C | 10C | 5C,9G | 4G | 1C,2G | 8G | 8G |
| Crabgrass | 7G | 2G | 4C,8G | 2C,6G | 0 | 2G | 2C | 0 |
| Downy brome | — | — | — | — | — | — | — | — |
| Giant foxtail | 9G | 7G | 3C,9G | 3C,7G | 2C,7G | 2G | 3C,6G | 3G |
| Morningglory | 10C | 9C | 10C | 9C | 5C,9G | 4C,9G | 10C | 9C |
| Nutsedge | 3C,8G | 5G | 5C,9G | 3C,8G | 3G | 0 | 0 | 0 |
| Rice | 6G | 6G | 3C,7G | 3G | 3G | 0 | 2C,6G | 0 |
| Sorghum | 5C,9G | 2C,9G | 4C,9G | 4C,9G | 4C,9G | 4C,9G | 4C,9G | 4C,8G |
| Soybean | 4C,8H | 3C,7H | 4C,9G | 4C,9G | 3C,8H | 4C,9G | 5C,9G | 3C,6G |
| Sugar beet | 9C | 4C,9G | 9C | 9C | 9C | 5C,9G | 9C | 9C |
| Velvetleaf | 9C | 10C | 10C | 4C,8G | 7G | 1C | 9C | 7G |
| Wheat | 2G | 0 | 4G | 0 | 0 | 0 | 2G | 0 |
| Wild oat | 2C,5G | 0 | 3C,6G | 4G | 0 | 0 | 0 | 0 |
| PREEMERGENCE | | | | | | | | |
| Barley | 2G | 0 | 2C,4G | 0 | 0 | 0 | 0 | 0 |
| Barnyardgrass | 9H | 2C,3G | 9H | 3C,8H | 3C,6H | 2G | 4C,9H | 2C,2H |
| Cheatgrass | 8G | 5G | 2C,7G | 5G | 3G | 0 | 7G | 6G |
| Cocklebur | 8H | 2C,5G | 9H | 2C,2H | 3C,8H | 1H | 2G | 0 |
| Corn | 2C,9H | 2C,3G | 3C,9G | 2C,6G | 3C,8G | 2G | 4C,7G | 2C,2G |
| Cotton | 8G | 2G | 3C,7H | 3G | 2C,7G | 2G | 4G | 0 |
| Crabgrass | 8G | 3G | 2C,9H | 8H | 8H | 0 | 2C,3G | 0 |
| Downy brome | — | — | — | — | — | — | — | — |
| Giant foxtail | 8H | 5G | 9H | 8H | 5G | 0 | 3C,7G | 2G |
| Morningglory | 9G | 2C,5H | 3C,7G | 5G | 3C,8H | 0 | 2C,3G | 0 |
| Nutsedge | 8G | 0 | 0 | 5G | 0 | 0 | 0 | 0 |
| Rice | 7G | 0 | 7G | 3G | 0 | 2G | 2C,2G | 0 |
| Sorghum | 9G | 2C,8G | 2C,9H | 3C,7G | 4C,9G | 8G | 2C,7G | 2C,4G |
| Soybean | 8H | 7H | 4C,8H | 3C,7H | 2C,3H | 0 | 2C,4G | 0 |
| Sugar beet | 9G | 9G | 4C,9G | 3C,8G | 4C,9G | 7G | 4C,9G | 6G |
| Velvetleaf | 8G | 3H | 3C,7H | 2C,2H | 3C,6H | 1H | 3C,6H | 2H |
| Wheat | 0 | 0 | 4G | 0 | 0 | 0 | 0 | 0 |
| Wild oat | 0 | 0 | 2C,5G | 1C | 0 | 0 | 0 | 0 |

| | Cmpd 9 | | Cmpd 10 | | Cmpd 11 | | Cmpd 12 | |
|---|---|---|---|---|---|---|---|---|
| RATE (g/ha) | 50 | 10 | 50 | 10 | 50 | 10 | 50 | 10 |
| POSTEMERGENCE | | | | | | | | |
| Barley | 0 | 0 | 3C,6G | 3G | 0 | 0 | 0 | 0 |
| Barnyardgrass | 3C,9H | 3C,7H | 9G | 4C,9H | 5G | 0 | 3C,9H | 6H |
| Cheatgrass | 7G | 3G | 4C,9G | 3C,8G | 0 | 0 | 7G | 4G |
| Cocklebur | 4C,9G | 2C,8H | 10C | 4C,9G | 4C,9G | 3C,7H | 4C,9G | 3C,9H |
| Corn | 2C,3G | 0 | 3C,9H | 3C,7H | 2C,5G | 0 | 2C,9G | 2G |
| Cotton | 10C | 3C,9G | 9C | 5C,9G | 3C,9G | 9G | 9C | 9G |
| Crabgrass | 3C,6G | 2G | 3G | 0 | 0 | 0 | 3G | 2G |
| Downy brome | — | — | — | — | — | — | — | |

TABLE A-continued

| | | | | | | | | |
|---|---|---|---|---|---|---|---|---|
| Giant foxtail | 6G | 4G | 2C,8G | 4G | 0 | 0 | 5G | 2G |
| Morningglory | 9C | 4C,9G | 9C | 4C,9H | 3C,9G | 2C,3H | 4C,9G | 3C,7H |
| Nutsedge | 9G | 2C,9G | 9G | 2C,8G | 0 | 0 | 8G | 4G |
| Rice | 2G | 0 | 4G | 0 | 0 | 0 | 0 | 0 |
| Sorghum | 3C,5G | 3G | 4C,9G | 3C,7G | 0 | 0 | 2C,6G | 2G |
| Soybean | 3C,9G | 2C,8G | 3C,9G | 4C,9G | 3C,7G | 1C,3H | 3C,7G | 1C,4G |
| Sugar beet | 9C | 4C,9G | 5C,9G | 9C | 3C,7H | 3C,6H | 5C,9H | 4C,8H |
| Velvetleaf | 9C | 8G | 6C,9G | 3C,8G | 4C,9H | 3C,8H | 5C,9H | 5H |
| Wheat | 0 | 0 | 7G | 3G | 0 | 0 | 0 | 0 |
| Wild oat | 0 | 0 | 2C,7G | 2C,3G | 0 | 0 | 2G | 0 |
| PREEMERGENCE | | | | | | | | |
| Barley | 0 | 0 | 4G | 2G | 0 | 0 | 0 | 0 |
| Barnyardgrass | 7G | 0 | 3C,8G | 2C,7H | 2G | 0 | 3C,7H | 3H |
| Cheatgrass | 7G | 0 | 2C,7G | 7G | 4G | 0 | 8G | 4G |
| Cocklebur | 7G | 0 | 7G | 1H | 7G | 0 | 3C,5G | 2G |
| Corn | 3C,7G | 2C,3G | 2C,8G | 3C,4G | 2C,3G | 0 | 2C,7G | 1C |
| Cotton | 3G | 0 | 3C,7G | 2G | 0 | 0 | 2G | 0 |
| Crabgrass | 0 | 0 | 3G | 0 | 0 | 0 | 2G | 0 |
| Downy brome | — | — | — | — | — | — | — | — |
| Giant foxtail | 2G | 0 | 5G | 0 | 0 | 0 | 3G | 2G |
| Morningglory | 8G | 2G | 8G | 4G | 9G | 2C,5G | 3C,9G | 2C,5G |
| Nutsedge | 3C,8G | 0 | 5G | 0 | 0 | 0 | 0 | 0 |
| Ric | 0 | 0 | 3G | 0 | 0 | 0 | 0 | 0 |
| Sorghum | 2C,2G | 0 | 3C,7G | 2C,3G | 5G | 4G | 4G | 2C,3G |
| Soybean | 3C,7H | 0 | 3C,8H | 2C,6G | 2C,4G | 1C,2G | 3C,6H | 2C,2H |
| Sugar beet | 8G | 5G | 4C,9G | 5G | 6G | 3G | 4C,8G | 4H |
| Velvetleaf | 7G | 2G | 4C,9G | 3G | 2C,7G | 2C,4G | 4C,8H | 3C,6H |
| Wheat | 0 | 0 | 2G | 0 | 0 | 0 | 0 | 0 |
| Wild oat | 0 | 0 | 4G | 0 | 0 | 0 | 2G | 0 |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria* spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. Plant response ratings, summarized in Table B, are based on a scale of 0 to 100 where 0 is no effect and 100 is complete control. A dash (-) response means no test result.

TABLE B

| | Cmpd 1 | | | | Compd 2 | | | | Compd 3 | | | | Compd 4 | | | |
|---|---|---|---|---|---|---|---|---|---|---|---|---|---|---|---|---|
| RATE (g/ha) | 62 | 16 | 4 | 1 | 62 | 16 | 4 | 1 | 250 | 62 | 16 | 4 | 62 | 16 | 4 | 1 |
| POSTEMERGENCE | | | | | | | | | | | | | | | | |
| Barley | 50 | 30 | 0 | 0 | 30 | 0 | 0 | 0 | 80 | 70 | 50 | 30 | 40 | 20 | 0 | 0 |
| Barnyardgrass | 100 | 100 | 80 | 60 | 100 | 100 | 90 | 60 | 100 | 100 | 90 | 80 | 100 | 80 | 70 | 40 |
| Blackgrass | 50 | 30 | 0 | 0 | 100 | 50 | 30 | 0 | 100 | 100 | 70 | 50 | 80 | 60 | 30 | 0 |
| Chickweed | 100 | 90 | 80 | 50 | 100 | 100 | 80 | 40 | 100 | 100 | 100 | 100 | 90 | 90 | 70 | 50 |
| Cocklebur | 100 | 100 | 90 | 60 | 100 | 100 | 80 | 60 | 100 | 100 | 100 | 100 | 80 | 70 | 60 | 20 |
| Corn | 70 | 60 | 50 | 30 | 90 | 80 | 70 | 30 | 100 | 100 | 100 | 100 | 100 | 50 | 20 | 0 |
| Cotton | 100 | 100 | 70 | 30 | 90 | 80 | 60 | 40 | 100 | 100 | 100 | 100 | 80 | 70 | 40 | 0 |
| Crabgrass | 80 | 60 | 30 | 0 | 80 | 50 | 30 | 0 | 90 | 70 | 50 | 40 | 90 | 70 | 30 | 0 |
| Downy brome | 70 | 50 | 30 | 0 | 70 | 50 | 30 | 0 | 70 | 60 | 50 | 30 | 50 | 20 | 0 | 0 |
| Giant foxtail | 100 | 70 | 50 | 30 | 90 | 70 | 50 | 30 | 90 | 80 | 70 | 60 | — | — | — | — |
| Green foxtail | 90 | 70 | 60 | 50 | 90 | 80 | 70 | 50 | 100 | 100 | 90 | 80 | 80 | 40 | 20 | 0 |
| Jimsonweed | 100 | 100 | 80 | 70 | 100 | 100 | 70 | 50 | 100 | 100 | 90 | 70 | 90 | 80 | 30 | 0 |
| Johnsongrass | 100 | 100 | 80 | 70 | 90 | 80 | 60 | 30 | 100 | 100 | 90 | 70 | — | — | — | — |
| Lambsquarters | 100 | 100 | 100 | 70 | 100 | 90 | 80 | 70 | 100 | 90 | 80 | 70 | 100 | 80 | 50 | 0 |
| Morningglory | 100 | 100 | 100 | 70 | 100 | 100 | 90 | 70 | 100 | 100 | 100 | 100 | 90 | 80 | 60 | — |
| Nutsedge | 100 | 90 | 50 | 0 | 70 | 50 | 30 | 0 | — | — | — | — | 0 | 0 | 0 | 0 |
| Rape | 100 | 100 | 100 | 100 | 100 | 100 | 100 | 100 | 100 | 100 | 100 | 100 | 100 | 100 | 100 | 90 |
| Rice | 90 | 60 | 0 | 0 | 70 | 50 | 30 | 0 | 70 | 60 | 50 | 30 | 80 | 30 | 30 | 20 |
| Sicklepod | 100 | 100 | 70 | 30 | 90 | 70 | 50 | 30 | 100 | 100 | 90 | 60 | 90 | 60 | 30 | 0 |
| Soybean | 90 | 80 | 70 | 60 | 100 | 100 | 80 | 60 | 100 | 100 | 100 | 80 | 80 | 60 | 40 | 30 |
| Sugar beet | 100 | 100 | 100 | 90 | 100 | 100 | 100 | 100 | 100 | 100 | 100 | 100 | 100 | 100 | 100 | 100 |
| Teaweed | 100 | 100 | 50 | 30 | 90 | 70 | 50 | 30 | 100 | 90 | 80 | 70 | 80 | 50 | 20 | 0 |
| Velvetleaf | 100 | 90 | 70 | 50 | 90 | 80 | 70 | 50 | 100 | 100 | 100 | 90 | 100 | 60 | 20 | 0 |
| Wheat | 30 | 0 | 0 | 0 | 50 | 30 | 0 | 0 | 50 | 30 | 0 | 0 | 50 | 10 | 0 | 0 |
| Wild buckwheat | 100 | 100 | 90 | 60 | 90 | 60 | 0 | 0 | 90 | 80 | 70 | 40 | 90 | 50 | 50 | 0 |
| Wild oat | 20 | 0 | 0 | 0 | 50 | 30 | 0 | 0 | 70 | 60 | 40 | 20 | 60 | 40 | 20 | 0 |

TABLE B-continued

| | Cmpd 1 | | | | Compd 2 | | | | Compd 3 | | | | Compd 4 | | | |
|---|---|---|---|---|---|---|---|---|---|---|---|---|---|---|---|---|
| RATE (g/ha) | 250 | 62 | 16 | 4 | 250 | 62 | 16 | 4 | 250 | 62 | 16 | 4 | 250 | 62 | 16 | 4 |
| PREEMERGENCE | | | | | | | | | | | | | | | | |
| Barley | 50 | 30 | 0 | 0 | 50 | 30 | 0 | 0 | 50 | 50 | 40 | 0 | 50 | 40 | 40 | 20 |
| Barnyardgrass | 100 | 100 | 80 | 50 | 100 | 100 | 80 | 50 | 100 | 100 | 90 | 20 | 100 | 90 | 90 | 50 |
| Blackgrass | 70 | 50 | 30 | 0 | 80 | 50 | 30 | 0 | 100 | 80 | 70 | 50 | 80 | 60 | 40 | 30 |
| Chickweed | 100 | 90 | 70 | 50 | 100 | 100 | 80 | 50 | 100 | 100 | 80 | 70 | 100 | 90 | 80 | 60 |
| Cocklebur | 90 | 70 | 50 | 30 | 90 | 80 | 30 | 0 | 100 | 100 | 100 | 80 | 90 | 90 | 85 | 0 |
| Corn | 100 | 100 | 0 | 0 | 90 | 60 | 0 | 0 | 100 | 100 | 100 | 40 | 100 | 100 | 100 | 90 |
| Cotton | 90 | 60 | 30 | 0 | 80 | 30 | 0 | 0 | 100 | 100 | 80 | 40 | 100 | 100 | 100 | 0 |
| Crabgrass | 90 | 80 | 50 | 30 | 90 | 80 | 70 | 60 | 100 | 100 | 80 | 70 | 100 | 100 | 90 | 80 |
| Downy brome | 70 | 50 | 30 | 0 | 70 | 50 | 30 | 0 | 70 | 30 | 0 | 0 | 40 | 0 | 0 | 0 |
| Giant foxtail | 90 | 80 | 70 | 30 | 100 | 90 | 70 | 50 | 100 | 80 | 60 | 30 | 100 | 90 | 80 | 30 |
| Green foxtail | 100 | 100 | 90 | 60 | 100 | 90 | 80 | 60 | 100 | 100 | 100 | 30 | 100 | 100 | 80 | 70 |
| Jimsonweed | 90 | 70 | 50 | 30 | 90 | 70 | 50 | 30 | 100 | 100 | 100 | 40 | 100 | 100 | 90 | 10 |
| Johnsongrass | 100 | 90 | 80 | 70 | 100 | 90 | 80 | 60 | 100 | 100 | 80 | 60 | 100 | 90 | 80 | 70 |
| Lambsquarters | 100 | 90 | 70 | 50 | 100 | 90 | 60 | 30 | 100 | 100 | 100 | 20 | 100 | 100 | 90 | 0 |
| Morningglory | 90 | 80 | 50 | 30 | 80 | 60 | 30 | 0 | 100 | 100 | 100 | 90 | 100 | 100 | 100 | 80 |
| Nutsedge | 90 | 60 | 30 | 0 | 30 | 0 | 0 | 0 | 100 | 0 | 0 | 0 | 80 | 20 | — | 0 |
| Rape | 100 | 100 | 90 | 70 | 100 | 90 | 70 | 50 | 100 | 100 | 100 | 90 | 100 | 100 | 100 | 90 |
| Rice | 70 | 50 | 30 | 0 | 70 | 50 | 0 | 0 | 90 | 80 | 60 | 50 | 100 | 70 | 50 | 30 |
| Sicklepod | 90 | 60 | 30 | 0 | 70 | 60 | 50 | 30 | 100 | 100 | 40 | 30 | 100 | 85 | 30 | 20 |
| Soybean | 90 | 70 | 30 | 0 | 90 | 60 | 30 | 0 | 100 | 60 | 50 | 0 | 100 | 80 | — | 40 |
| Sugar beet | 100 | 90 | 80 | 70 | 100 | 90 | 80 | 60 | 100 | 100 | 100 | 100 | 100 | 100 | 100 | 80 |
| Teaweed | 90 | 70 | 50 | 30 | 90 | 60 | 30 | 0 | 100 | 100 | 90 | 0 | 100 | 90 | 80 | 60 |
| Velvetleaf | 90 | 80 | 70 | 60 | 90 | 70 | 50 | 30 | 100 | 100 | 80 | 30 | 90 | 90 | 70 | 30 |
| Wheat | 30 | 0 | 0 | 0 | 50 | 30 | 0 | 0 | 40 | 30 | 20 | 0 | 20 | 20 | 0 | 0 |
| Wild buckwheat | 100 | 100 | 70 | 30 | 90 | 70 | 50 | 30 | 100 | 100 | 90 | 70 | 90 | 80 | 0 | 0 |
| Wild oat | 50 | 30 | 0 | 0 | 70 | 50 | 30 | 0 | 60 | 50 | 0 | 0 | 45 | 40 | 30 | 30 |

| | Compd 5 | | | | Compd 6 | | | | Cmpd 10 | | | | Cmpd 12 | | | |
|---|---|---|---|---|---|---|---|---|---|---|---|---|---|---|---|---|
| RATE (g/ha) | 62 | 16 | 4 | 1 | 62 | 16 | 4 | 1 | 250 | 62 | 16 | 4 | 250 | 62 | 16 | 4 |
| POSTEMERGENCE | | | | | | | | | | | | | | | | |
| Barley | 50 | 30 | 0 | 0 | 60 | 20 | 0 | 0 | 60 | 40 | 20 | 0 | 50 | 40 | 0 | 0 |
| Barnyardgrass | 100 | 90 | 80 | 50 | 100 | 90 | 80 | — | 100 | 90 | 70 | 40 | 90 | 60 | 50 | 30 |
| Blackgrass | 100 | 80 | 50 | 0 | 80 | 70 | 50 | 40 | 100 | 70 | 50 | 30 | 80 | 50 | 30 | 0 |
| Chickweed | 100 | 100 | 50 | 0 | 100 | 90 | 70 | 30 | 100 | 90 | 50 | 0 | 100 | 50 | 40 | 0 |
| Cocklebur | 100 | 100 | 100 | 30 | 100 | 100 | 100 | — | 100 | 100 | 80 | 70 | 100 | 100 | 90 | 50 |
| Corn | 100 | 90 | 50 | 0 | 90 | 85 | 60 | — | 80 | 60 | 40 | 0 | 85 | 50 | 20 | 0 |
| Cotton | 100 | 100 | 90 | 60 | 100 | 90 | 90 | — | 100 | 100 | 100 | 60 | 100 | 90 | 90 | 40 |
| Crabgrass | 70 | 50 | 40 | 0 | 70 | 50 | 40 | 20 | 40 | 30 | 0 | 0 | 50 | 30 | 0 | 0 |
| Downy brome | 30 | 30 | 0 | 0 | 60 | 30 | 0 | 0 | 70 | 50 | 30 | 0 | 30 | 0 | 0 | 0 |
| Giant foxtail | 80 | 50 | 30 | 0 | 90 | 70 | 0 | — | 90 | 70 | 50 | 30 | 30 | 0 | 0 | 0 |
| Green foxtail | 90 | 80 | 50 | 20 | 100 | 90 | 40 | — | 90 | 60 | 30 | 0 | 60 | 20 | 0 | 0 |
| Jimsonweed | 100 | 100 | 70 | 50 | 100 | 100 | 60 | 50 | 100 | 90 | 80 | 50 | 100 | 40 | 30 | 30 |
| Johnsongrass | 90 | 85 | 70 | 60 | 100 | 70 | 50 | — | 100 | 100 | 80 | 50 | 90 | 90 | 20 | 0 |
| Lambsquarters | 80 | 60 | 30 | 0 | 90 | 30 | 20 | 0 | 100 | 70 | 50 | 30 | 100 | 80 | 20 | 0 |
| Morningglory | 100 | 100 | 90 | — | 100 | 90 | 80 | — | 100 | 100 | 100 | 70 | 100 | 100 | 100 | 80 |
| Nutsedge | 90 | 70 | 50 | 30 | 90 | 30 | — | 0 | 100 | 90 | 70 | 50 | 100 | 90 | 20 | 0 |
| Rape | 100 | 100 | 100 | 100 | 100 | 100 | 100 | 80 | 100 | 100 | 100 | 100 | 100 | 100 | 100 | 100 |
| Rice | 80 | 60 | 50 | 0 | 80 | 50 | 40 | 30 | 70 | 50 | 30 | 0 | 50 | 30 | 0 | 0 |
| Sicklepod | 80 | 70 | 60 | 0 | 90 | 30 | 30 | 0 | 80 | 70 | 60 | 30 | 100 | 90 | 50 | 50 |
| Soybean | 100 | 100 | 90 | 50 | 100 | 100 | 90 | — | 100 | 100 | 70 | 60 | 100 | 90 | 80 | 60 |
| Sugar beet | 100 | 100 | 100 | 90 | 100 | 100 | 100 | 90 | 100 | 100 | 100 | 80 | 100 | 100 | 100 | 100 |
| Teaweed | 80 | 60 | 55 | 0 | 90 | 80 | 0 | 0 | 70 | 60 | 30 | 0 | 60 | 40 | 30 | 20 |
| Velvetleaf | 100 | 100 | 80 | 60 | 100 | 100 | 60 | 50 | 100 | 100 | 100 | 60 | 100 | 100 | 100 | 80 |
| Wheat | 40 | 20 | 0 | 0 | 50 | 30 | 0 | 0 | 50 | 30 | 0 | 0 | 30 | 0 | 0 | 0 |
| Wild buckwheat | 100 | 90 | 30 | 0 | 100 | 80 | 40 | 0 | 90 | 80 | 60 | 30 | 90 | 90 | 50 | 0 |
| Wild oat | 70 | 50 | 0 | 0 | 90 | 30 | 0 | 0 | 70 | 60 | 30 | 0 | 40 | — | 0 | 0 |

| | Compd 5 | | | | Compd 6 | | | | Cmpd 10 | | | | Cmpd 12 | | | |
|---|---|---|---|---|---|---|---|---|---|---|---|---|---|---|---|---|
| RATE (g/ha) | 250 | 62 | 16 | 4 | 250 | 62 | 16 | 4 | 250 | 62 | 16 | 4 | 250 | 62 | 16 | 4 |
| PREEMERGENCE | | | | | | | | | | | | | | | | |
| Barley | 40 | 0 | 0 | 0 | 30 | 0 | 0 | 0 | 30 | 0 | 0 | 0 | 0 | 0 | 0 | 0 |
| Barnyardgrass | 80 | 60 | 50 | 0 | 80 | 70 | 60 | 30 | 100 | 90 | 70 | 50 | 90 | 50 | 0 | 0 |
| Blackgrass | 70 | 50 | 50 | 30 | 80 | 70 | 70 | 50 | 80 | 70 | 50 | 30 | 70 | 50 | 30 | 0 |
| Chickweed | 90 | 80 | 80 | 80 | 90 | 80 | 70 | 60 | 90 | 60 | 30 | 0 | 70 | 50 | 40 | 30 |
| Cocklebur | 80 | 80 | 50 | — | 70 | 70 | 60 | 30 | 90 | 80 | 30 | 0 | 70 | 50 | 0 | 0 |
| Corn | 90 | 60 | 0 | 0 | 100 | 70 | 0 | 0 | 90 | 40 | 20 | 0 | 80 | 40 | 0 | 0 |
| Cotton | 70 | 60 | 30 | 0 | 60 | 30 | 0 | 0 | 60 | 30 | 0 | 0 | 50 | 20 | 0 | 0 |
| Crabgrass | 85 | 80 | 70 | 60 | 100 | 90 | 80 | 70 | 90 | 80 | 50 | 0 | 100 | 70 | 30 | 0 |
| Downy brome | 30 | 0 | 0 | 0 | 30 | 0 | 0 | 0 | 50 | 30 | 0 | 0 | 50 | 30 | 0 | 0 |
| Giant foxtail | 80 | 60 | 30 | 0 | 80 | 70 | 60 | 0 | 100 | 90 | 40 | 20 | 50 | 30 | 0 | 0 |
| Green foxtail | 90 | 80 | 50 | 30 | 90 | 90 | 70 | 40 | 90 | 80 | 50 | 0 | 80 | 50 | 30 | 0 |
| Jimsonweed | 80 | 60 | 40 | 30 | 90 | 80 | 70 | 30 | 90 | 80 | 60 | 40 | 70 | 60 | 50 | 30 |
| Johnsongrass | 70 | 60 | 30 | 0 | 80 | 70 | 60 | 40 | 90 | 80 | 70 | 30 | 80 | 70 | 30 | 0 |
| Lambsquarters | 95 | 90 | 80 | 50 | 100 | 95 | 80 | 70 | 100 | 90 | 80 | 70 | 90 | 80 | 70 | 30 |
| Morningglory | 70 | 60 | 60 | 40 | 80 | 60 | 30 | 0 | 90 | 80 | 70 | 60 | 80 | 50 | 30 | 0 |
| Nutsedge | 70 | 50 | 0 | 0 | 30 | 30 | 30 | 0 | 100 | 90 | 60 | 30 | — | — | — | — |
| Rape | 90 | 80 | 60 | 40 | 80 | 70 | 60 | 40 | 90 | 80 | 70 | 40 | 90 | 80 | 70 | 60 |

TABLE B-continued

| | | | | | | | | | | | | | | | | |
|---|---|---|---|---|---|---|---|---|---|---|---|---|---|---|---|---|
| Rice | 90 | 60 | 40 | 0 | 70 | 60 | 30 | 0 | 90 | 60 | 30 | 0 | 50 | 0 | 0 | 0 |
| Sicklepod | 90 | 80 | 70 | 60 | 70 | 70 | 70 | 70 | 90 | 80 | 60 | 40 | 90 | 70 | 30 | 0 |
| Soybean | 60 | 20 | 0 | 0 | 60 | 40 | 20 | 0 | 70 | 50 | 30 | 0 | 70 | 50 | 20 | 0 |
| Sugar beet | 80 | 75 | 70 | 50 | 90 | 90 | 70 | 70 | 80 | 70 | 50 | 30 | 90 | 70 | 30 | 0 |
| Teaweed | 100 | 80 | 70 | 60 | 70 | 60 | 50 | 40 | 90 | 60 | 30 | 0 | 70 | 60 | 50 | 30 |
| Velvetleaf | 80 | 70 | 50 | 30 | 80 | 70 | 60 | 30 | 90 | 80 | 60 | 30 | 80 | 70 | 30 | 0 |
| Wheat | 0 | 0 | 0 | 0 | 40 | 0 | 0 | 0 | 60 | 30 | 0 | 0 | 0 | 0 | 0 | 0 |
| Wild buckwheat | 90 | 70 | 50 | 30 | 80 | 60 | 30 | 0 | 90 | 70 | 30 | 0 | 60 | 30 | 0 | 0 |
| Wild oat | 40 | 30 | 30 | 0 | 60 | 30 | 0 | 0 | 70 | 60 | 50 | 40 | 0 | 0 | 0 | 0 |

TEST C

Plastic pots were partially filled with silt loam soil. The soil was then saturated with water. Japonica and Indica rice (*Oryza sativa*) seedlings at the 2.0 to 2.5 leaf stage, seeds selected from barnyardgrass (*Echinochloa crus-galli*), bulrush (*Scirous mucronatus*), duck salad (*Heteranthera limosa*), scirpus (*Scirpus* spp.), umbrella sedge (*Cyperus difformis*), and water plantain (*Alisma triviale*), and tubers selected from arrowhead (*Sagittaria rigida*), common arrowhead (*Sagittaria latifolia*), waterchestnut (*Eleocharis* spp.), and yellow nutsedge (*Cyperus esculentus*) were planted into this soil. Several days after planting, water levels were raised to 3 cm above the soil surface and maintained at this level throughout the test. Chemical treatments were formulated in a nonphytotoxic solvent and applied directly to the paddy water. Treated plants and controls were maintained in a greenhouse for approximately 21 days, after which all species were compared to controls and visually evaluated. Plant response ratings, summarized in Table C, are based on a scale of 0 to 100 where 0 is no effect and 100 is complete control. A dash (-) response means no test result.

TABLE C

| | Cmpd 1 | | | | | Cmpd 2 | | | | | Cmpd 3 | | | |
|---|---|---|---|---|---|---|---|---|---|---|---|---|---|---|
| RATE (g/ha) | 250 | 125 | 64 | 32 | 16 | 32 | 16 | 8 | 4 | 8 | 4 | 2 | 1 | 0.5 |
| Arrowhead | — | — | — | — | — | — | — | — | — | — | — | — | — | — |
| Barnyardgrass | 100 | 100 | 100 | 100 | 95 | 100 | 100 | 95 | 70 | 80 | 50 | 30 | 0 | 0 |
| Bulrush | — | — | — | — | — | 90 | 90 | 90 | 80 | 95 | 95 | 80 | 0 | 0 |
| Common Arrowhead | 100 | 100 | 95 | 50 | 0 | — | — | — | — | — | — | — | — | — |
| Duck salad | — | — | — | — | — | 100 | 100 | 100 | 95 | 100 | 100 | 100 | 0 | 0 |
| Rice (Indica) | 30 | 20 | 0 | 0 | 0 | 0 | 10 | 0 | 0 | 30 | 20 | 0 | 0 | 0 |
| Rice (Japonica) | 40 | 30 | 20 | 20 | 0 | 25 | 20 | 0 | 0 | 50 | 30 | 0 | 0 | 0 |
| Scirpus | 100 | 100 | 95 | 95 | 90 | — | — | — | — | — | — | — | — | — |
| Umbrella sedge | — | — | — | — | — | 100 | 100 | 100 | 95 | 100 | 100 | 95 | 80 | 60 |
| Water Plantain | 100 | 100 | 95 | 95 | 90 | — | — | — | — | — | — | — | — | — |
| Waterchestnut | 95 | 95 | 90 | 80 | 75 | 95 | 95 | 95 | 80 | 90 | 80 | 80 | 60 | 0 |
| Yellow Nutsedge | 95 | 75 | 45 | 0 | 0 | — | — | — | — | — | — | — | — | — |

| | Cmpd 5 | | | | | Cmpd 6 | | | | | Cmpd 7 | | | |
|---|---|---|---|---|---|---|---|---|---|---|---|---|---|---|
| RATE (g/ha) | 64 | 32 | 16 | 8 | 4 | 64 | 32 | 16 | 8 | 4 | 125 | 64 | 32 | 16 | 8 |
| Arrowhead | 90 | 70 | 60 | 0 | 0 | 90 | 90 | 90 | 90 | 70 | 95 | 95 | 95 | 60 | 0 |
| Barnyardgrass | 100 | 90 | 80 | 30 | 30 | 100 | 100 | 95 | 80 | 60 | 95 | 80 | 60 | 0 | 0 |
| Bulrush | 80 | 70 | 70 | 60 | 50 | 80 | 80 | 80 | 80 | 70 | 98 | 95 | 90 | 60 | 0 |
| Common Arrowhead | — | — | — | — | — | — | — | — | — | — | — | — | — | — | — |
| Duck salad | 0 | 0 | 100 | 100 | 100 | 100 | 100 | 100 | 100 | 100 | 100 | 100 | 100 | 100 | 100 |
| Rice (Indica) | 0 | 0 | 0 | 0 | 0 | 50 | 40 | 30 | 20 | 0 | 20 | 0 | 0 | 0 | 0 |
| Rice (Japonica) | 40 | 0 | 0 | 0 | 0 | 60 | 50 | 30 | 0 | 0 | 30 | 20 | 0 | 0 | 0 |
| Scirpus | — | — | — | — | — | — | — | — | — | — | — | — | — | — | — |
| Umbrella sedge | 100 | 100 | 100 | 95 | 80 | 100 | 100 | 100 | 95 | 70 | 100 | 98 | 80 | 60 | 0 |
| Water Plantain | — | — | — | — | — | — | — | — | — | — | — | — | — | — | — |
| Waterchestnut | 80 | 40 | 70 | 0 | 0 | 80 | 80 | 70 | 70 | 60 | 95 | 95 | 90 | 70 | 70 |
| Yellow Nutsedge | — | — | — | — | — | — | — | — | — | — | — | — | — | — | — |

| | Cmpd 9 | | | | | Cmpd 10 | | | | |
|---|---|---|---|---|---|---|---|---|---|---|
| RATE (g/ha) | 125 | 64 | 32 | 16 | 8 | 125 | 64 | 32 | 16 | 8 |
| Arrowhead | 100 | 90 | 90 | 80 | 70 | 100 | 100 | 100 | 95 | 95 |
| Barnyardgrass | 98 | 95 | 60 | 50 | 30 | 100 | 100 | 90 | 65 | 20 |
| Bulrush | 95 | 90 | 90 | 98 | 80 | 100 | 95 | 95 | 95 | 95 |
| Common Arrowhead | — | — | — | — | — | — | — | — | — | — |
| Duck salad | — | — | — | — | — | — | — | — | — | — |
| Rice (Indica) | 20 | 0 | 0 | 0 | 0 | 35 | 20 | 20 | 10 | 0 |
| Rice (Japonica) | 20 | 0 | 0 | 0 | 0 | 50 | 40 | 20 | 10 | 0 |
| Scirpus | — | — | — | — | — | — | — | — | — | — |
| Umbrella sedge | 100 | 100 | 100 | 98 | 95 | — | — | — | — | — |
| Water Plantain | 100 | 100 | 100 | 100 | 90 | 100 | 100 | 95 | 95 | 95 |
| Waterchestnut | 80 | 80 | 70 | 70 | 70 | 85 | 75 | 40 | 40 | 40 |
| Yellow Nutsedge | — | — | — | — | — | 100 | 90 | 80 | 60 | 40 |

TEST D

Seeds of spring and winter barley (*Hordeum vulgare*), black nightshade (*Solanum nigrum*), blackgrass (*Alopecurus myosuroides*), bluegrass (*Poa annua*), catchweed bedstraw (*Galium aparine*), cheatgrass (*Bromus secalinus*), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hedersefolia*), jointed goatgrass (*Aegilops cylindrica*), kochia (*Kochia scoparia*), lambsquarters (*Chenopodium album*), Persian speedwell (*Veronica persica*), rape (*Brassica napus*), Russian thistle (*Salsola kali*), scentless chamomile (*Matricaria inodora*), sugar beet (*Beta vulgaris*), spring and winter wheat (*Triticum aestivum*), wild buckwheat (*Polygonum convolvulus*), and wild oat (*Avena fatua*) were planted and treated preemergence with test chemicals dissolved in a non-phytotoxic solvent. At the same time, these crop and weed species were also treated with postemergence applications of test chemicals. Plants ranged in height from two to twenty-four cm (two to three leaf stage) for postemergence treatments. Blackgrass and wild oat were treated postemergence at two growth stages—the first stage being at two to three leaves and the second stage being approximately at four leaves or in the initial stages of tillering. Treated plants and controls were maintained in a greenhouse for approximately 21 days, after which all species were compared to controls and visually evaluated. Plant response ratings, summarized in Table D, are based on a scale of 0 to 100 where 0 is no effect and 100 is complete control. A dash (-) response means no test result.

TABLE D

|  | Cmpd 1 | | | | | | Cmpd 2 | | | | |
|---|---|---|---|---|---|---|---|---|---|---|---|
| RATE (g/ha) | 125 | 64 | 32 | 16 | 8 | 4 | 125 | 64 | 32 | 16 | 8 |
| POSTEMERGENCE | | | | | | | | | | | |
| Barley, Spring | 30 | 20 | 10 | 0 | 0 | 0 | 80 | 70 | 60 | 30 | 10 |
| Barley, Winter | 50 | 40 | 30 | 30 | 10 | 10 | 70 | 50 | 30 | 10 | 0 |
| Black nightshade | 50 | 50 | 50 | 40 | 10 | 0 | 0 | 0 | 0 | 0 | 0 |
| Blackgrass | 80 | 80 | 70 | 50 | 0 | 0 | 60 | 40 | 20 | 10 | 0 |
| Blackgrass, Stage 2 | 0 | 0 | 0 | 0 | 0 | 0 | 70 | 50 | 30 | 10 | 0 |
| Bluegrass | 40 | 40 | 30 | 10 | 0 | 0 | 30 | 10 | 0 | 0 | 0 |
| Catchweed bedstraw | 10 | 10 | 10 | 0 | 0 | 0 | 50 | 40 | 30 | 10 | 10 |
| Cheatgrass | 70 | 70 | 50 | 30 | 0 | 0 | 60 | 50 | 40 | 20 | 0 |
| Downy brome | 0 | 0 | 0 | 0 | 0 | 0 | 10 | 0 | 0 | 0 | 0 |
| Field pennycress | 60 | 40 | 30 | 10 | 0 | 0 | 100 | 100 | 100 | 100 | 80 |
| Field violet | 40 | 20 | 10 | 0 | 0 | 0 | 30 | 10 | 0 | 0 | 0 |
| Green foxtail | 90 | 90 | 90 | 70 | 50 | 20 | 80 | 50 | 40 | 20 | 0 |
| Italian ryegrass | 10 | 10 | 0 | 0 | 0 | 0 | 80 | 80 | 50 | 30 | 10 |
| Ivyleaf speedwell | 0 | 0 | 0 | 0 | 0 | 0 | 20 | 0 | 0 | 0 | 0 |
| Jointed goatgrass | 40 | 40 | 30 | 10 | 0 | 0 | 60 | 40 | 20 | 10 | 0 |
| Kochia | 70 | 60 | 60 | 40 | 30 | 0 | 100 | 100 | 100 | 80 | 60 |
| Lambsquarters | 80 | 80 | 70 | 70 | 50 | 20 | 100 | 90 | 70 | 50 | 50 |
| Persian speedwell | 0 | 0 | 0 | 0 | 0 | 0 | 40 | 10 | 0 | 0 | 0 |
| Rape | 100 | 100 | 100 | 100 | 100 | 100 | 100 | 100 | 100 | 100 | 100 |
| Russian thistle | — | — | — | — | — | — | 100 | 90 | 80 | 70 | 60 |
| Scentless chamomile | 30 | 20 | 20 | 0 | 0 | 0 | 100 | 100 | 100 | 100 | 100 |
| Sugar beet | 100 | 100 | 100 | 100 | 100 | 90 | 100 | 100 | 100 | 100 | 100 |
| Wheat, Spring | 0 | 0 | 0 | 0 | 0 | 0 | 50 | 40 | 40 | 20 | 0 |
| Wheat, Winter | 20 | 10 | 10 | 0 | 0 | 0 | 50 | 30 | 20 | 10 | 0 |
| Wild buckwheat | 80 | 60 | 50 | 30 | 20 | 0 | 60 | 40 | 10 | 0 | 0 |
| Wild oat | 10 | 0 | 0 | 0 | 0 | 0 | 70 | 40 | 20 | 0 | 0 |
| Wild oat, Stage 2 | 20 | 10 | 0 | 0 | 0 | 0 | 60 | 50 | 30 | 10 | 0 |
| PREEMERGENCE | | | | | | | | | | | |
| Barley, Spring | 40 | 40 | 30 | 30 | 0 | 0 | 70 | 50 | 40 | 20 | 0 |
| Barley, Winter | 70 | 50 | 40 | 20 | 10 | 0 | 60 | 60 | 50 | 30 | 10 |
| Black nightshade | 70 | 70 | 60 | 30 | 20 | 0 | 70 | 70 | 50 | 50 | 30 |
| Blackgrass | 90 | 80 | 60 | 60 | 40 | 20 | 80 | 80 | 60 | 40 | 20 |
| Bluegrass | 50 | 40 | 20 | 10 | 0 | 0 | 70 | 40 | 40 | 20 | 0 |
| Catchweed bedstraw | 90 | 80 | 50 | 30 | 10 | 0 | 90 | 70 | 50 | 50 | 10 |
| Cheatgrass | 80 | 60 | 30 | 0 | 0 | 0 | 80 | 70 | 40 | 40 | 20 |
| Downy brome | 30 | 10 | 10 | 0 | 0 | 0 | 60 | 50 | 20 | 0 | 0 |
| Field pennycress | 100 | 100 | 100 | 90 | 70 | 50 | 100 | 100 | 100 | 100 | 100 |
| Field violet | 60 | 50 | 20 | 10 | 0 | 0 | 100 | 100 | 80 | 70 | 30 |
| Green foxtail | 100 | 80 | 80 | 60 | 20 | 0 | 100 | 80 | 80 | 50 | 20 |
| Italian ryegrass | 70 | 40 | 40 | 30 | 10 | 0 | 80 | 80 | 60 | 50 | 20 |
| Ivyleaf speedwell | 80 | 30 | 0 | 0 | 0 | 0 | 100 | 100 | 80 | 60 | 40 |
| Jointed goatgrass | 30 | 10 | 0 | 0 | 0 | 0 | 50 | 30 | 10 | 0 | 0 |
| Kochia | 50 | 20 | 0 | 0 | 0 | 0 | 100 | 90 | 90 | 80 | 70 |
| Lambsquarters | 90 | 90 | 90 | 70 | 30 | 20 | 100 | 100 | 90 | 80 | 70 |
| Persian speedwell | 60 | 30 | 30 | 10 | 0 | 0 | 90 | 80 | 70 | 50 | |
| Rape | 100 | 100 | 100 | 100 | 60 | 40 | 100 | 100 | 100 | 100 | 90 |
| Russian thistle | — | — | — | — | — | — | 90 | 80 | 80 | 60 | 30 |
| Scentless chamomile | 100 | 100 | 90 | 90 | 80 | 70 | 100 | 100 | 100 | 90 | 80 |
| Sugar beet | 100 | 100 | 100 | 80 | 70 | 60 | 100 | 100 | 100 | 100 | 90 |
| Wheat, Spring | 10 | 0 | 0 | 0 | 0 | 0 | 60 | 60 | 40 | 20 | 0 |
| Wheat, Winter | 20 | 10 | 10 | 0 | 0 | 0 | 40 | 30 | 20 | 10 | 0 |
| Wild buckwheat | 80 | 80 | 50 | 30 | 10 | 0 | 90 | 90 | 70 | 60 | 50 |
| Wild oat | 20 | 20 | 0 | 0 | 0 | 0 | 50 | 30 | 20 | 10 | 0 |

|  | Cmpd 5 | | | | | Cmpd 12 | | | |
|---|---|---|---|---|---|---|---|---|---|
| RATE (g/ha) | 125 | 64 | 32 | 16 | 8 | 125 | 64 | 32 | 16 |
| POSTEMERGENCE | | | | | | | | | |
| Barley, Spring | 20 | 10 | 10 | 0 | 0 | 20 | 10 | 0 | 0 |
| Barley, Winter | 10 | 0 | 0 | 0 | 0 | 10 | 0 | 0 | 0 |
| Black nightshade | 70 | 70 | 70 | 40 | 30 | 10 | 0 | 0 | 0 |
| Blackgrass | 40 | 10 | 0 | 0 | 0 | 70 | 40 | 20 | 0 |
| Blackgrass, Stage 2 | 30 | 0 | 0 | 0 | 0 | 30 | 10 | 0 | 0 |
| Bluegrass | 0 | 0 | 0 | 0 | 0 | 10 | 0 | 0 | 0 |
| Catchweed bedstraw | 100 | 80 | 70 | 40 | 10 | 50 | 40 | 40 | 10 |
| Cheatgrass | 30 | 20 | 0 | 0 | 0 | 60 | 40 | 20 | 0 |

TABLE D-continued

|  |  |  |  |  |  |  |  |  |  |
|---|---|---|---|---|---|---|---|---|---|
| Downy brome | 0 | 0 | 0 | 0 | 0 | 0 | 0 | 0 | 0 |
| Field pennycress | 100 | 100 | 100 | 100 | 100 | 100 | 100 | 100 | 100 |
| Field violet | 30 | 10 | 0 | 0 | 0 | 0 | 0 | 0 | 0 |
| Green foxtail | 90 | 70 | 40 | 40 | 30 | 50 | 20 | 0 | 0 |
| Italian ryegrass | 40 | 10 | 0 | 0 | 0 | 80 | 60 | 50 | 40 |
| Ivyleaf speedwell | 100 | 100 | 90 | 70 | 50 | 40 | 40 | 20 | 0 |
| Jointed goatgrass | 20 | 10 | 0 | 0 | 0 | 30 | 10 | 0 | 0 |
| Kochia | 70 | 70 | 40 | 10 | 0 | 0 | 0 | 0 | 0 |
| Lambsquarters | 50 | 40 | 10 | 0 | 0 | 30 | 10 | 0 | 0 |
| Persian speedwell | 50 | 40 | 20 | 20 | 0 | 40 | 20 | 10 | 0 |
| Rape | 100 | 100 | 100 | 100 | 100 | 100 | 100 | 100 | 100 |
| Russian thistle | 100 | 100 | 100 | 100 | 90 | 90 | 70 | 60 | 30 |
| Scentless chamomile | 100 | 100 | 90 | 90 | 70 | 80 | 70 | 70 | 50 |
| Sugar beet | 100 | 100 | 100 | 100 | 100 | 100 | 100 | 100 | 90 |
| Wheat, Spring | 0 | 0 | 0 | 0 | 0 | 10 | 0 | 0 | 0 |
| Wheat, Winter | 0 | 0 | 0 | 0 | 0 | 10 | 0 | 0 | 0 |
| Wild buckwheat | 70 | 50 | 10 | 0 | 0 | 0 | 0 | 0 | 0 |
| Wild oat | 20 | 0 | 0 | 0 | 0 | 0 | 0 | 0 | 0 |
| Wild oat, Stage 2 | 0 | 0 | 0 | 0 | 0 | 0 | 0 | 0 | 0 |
| PREEMERGENCE |  |  |  |  |  |  |  |  |  |
| Barley, Spring | 30 | 10 | 10 | 0 | 0 | 40 | 20 | 10 | 0 |
| Barley, Winter | 30 | 10 | 0 | 0 | 0 | 20 | 10 | 0 | 0 |
| Black nightshade | 100 | 70 | 20 | 20 | 0 | 0 | 0 | 0 | 0 |
| Blackgrass | 80 | 70 | 50 | 40 | 20 | 70 | 40 | 10 | 0 |
| Bluegrass | 30 | 10 | 0 | 0 | 0 | 50 | 20 | 10 | 0 |
| Catchweed bedstraw | 80 | 80 | 50 | 10 | 0 | 40 | 40 | 10 | 0 |
| Cheatgrass | 80 | 80 | 60 | 50 | 20 | 70 | 60 | 30 | 20 |
| Downy brome | 0 | 0 | 0 | 0 | 0 | 20 | 10 | 0 | 0 |
| Field pennycress | 100 | 100 | 90 | 90 | 70 | 90 | 70 | 70 | 50 |
| Field violet | 90 | 90 | 90 | 50 | 30 | 0 | 0 | 0 | 0 |
| Green foxtail | 90 | 90 | 40 | 30 | 10 | 30 | 10 | 0 | 0 |
| Italian ryegrass | 30 | 10 | 0 | 0 | 0 | 80 | 70 | 50 | 30 |
| Ivyleaf speedwell | 80 | 70 | 70 | 50 | 20 | 70 | 40 | 10 | 0 |
| Jointed goatgrass | 20 | 0 | 0 | 0 | 0 | 30 | 10 | 0 | 0 |
| Kochia | 70 | 50 | 20 | 10 | 0 | 20 | 0 | 0 | 0 |
| Lambsquarters | 90 | 60 | 50 | 50 | 30 | 70 | 70 | 50 | 30 |
| Persian speedwell | 60 | 20 | 10 | 0 | 0 | 70 | 50 | 40 | 20 |
| Rape | 100 | 100 | 100 | 90 | 90 | 100 | 90 | 90 | 70 |
| Russian thistle | 20 | 10 | 0 | 0 | 0 | 80 | 60 | 50 | 0 |
| Scentless chamomile | 100 | 100 | 100 | 90 | 60 | 90 | 70 | 50 | 10 |
| Sugar beet | 100 | 100 | 90 | 90 | 70 | 100 | 100 | 90 | 90 |
| Wheat, Spring | 10 | 10 | 0 | 0 | 0 | 10 | 0 | 0 | 0 |
| Wheat, Winter | 10 | 0 | 0 | 0 | 0 | 20 | 10 | 0 | 0 |
| Wild buckwheat | 90 | 60 | 40 | 20 | 0 | 40 | 10 | 0 | 0 |
| Wild oat | 10 | 0 | 0 | 0 | 0 | 30 | 10 | 0 | 0 |

Seeds of alfalfa *Medicago sativa*), barley (*Hordeum vulgare*), bluegrass (*Poa pratensis*), corn (*Zea mays*), cotton (*Gossypium hirsutum*), oat (*Avena sativa*), peanut (*Arachis hypogaea*), peas (*Pisium sativum*), potato (*Solanum tuberosum*), rape (*Brassica napus*), rice (*Oryza sativa*), sorghum (*Sorghum bicolor*), soybean (*Glycine max*), sugar beet (*Beta vulgaris*), tomato (*Lycopersicon esculentum*), and wheat (*Triticum aestivum*) were planted into a sandy loam soil. These plants were allowed to grow to the two to three leaf stage (four to twenty cm) before they were treated postemergence with test chemicals dissolved in a non-phytotoxic solvent. Treated plants and controls were grown under greenhouse conditions for approximately twenty-four days, after which all treated plants were visually compared to untreated controls and evaluated for injury response. Plant response ratings, summarized in Table E, are from 0 to 100 where 0 is no injury and 100 is complete control.

TABLE E

|  | Cmpd 1 | | | | | | Cmpd 2 | | | | | |
|---|---|---|---|---|---|---|---|---|---|---|---|---|
| RATE (g/ha) | 125 | 64 | 32 | 16 | 8 | 4 | 125 | 64 | 32 | 16 | 8 | 4 |
| POSTEMERGENCE |  |  |  |  |  |  |  |  |  |  |  |  |
| Alfalfa | 100 | 95 | 85 | 65 | 50 | 25 | 100 | 95 | 85 | 65 | 40 | 35 |
| Barley, Spring | 60 | 40 | 30 | 0 | 0 | 0 | 75 | 65 | 40 | 30 | 0 | 0 |
| Bluegrass | 95 | 85 | 70 | 45 | 25 | 0 | 95 | 80 | 65 | 40 | 25 | 0 |
| Corn | 100 | 100 | 100 | 100 | 95 | 75 | 100 | 100 | 100 | 90 | 65 | 30 |
| Cotton | 100 | 100 | 100 | 95 | 80 | 60 | 100 | 100 | 100 | 95 | 65 | 35 |
| Oat | 50 | 35 | 25 | 0 | 0 | 0 | 80 | 70 | 40 | 25 | 0 | 0 |
| Peanut | 100 | 95 | 90 | 70 | 55 | 35 | 100 | 95 | 90 | 80 | 45 | 25 |
| Peas | 100 | 100 | 100 | 100 | 90 | 75 | 100 | 100 | 100 | 95 | 95 | 60 |
| Potato | 60 | 40 | 30 | 20 | 0 | 0 | 70 | 65 | 60 | 45 | 35 | 20 |
| Rape | 100 | 100 | 100 | 100 | 100 | 80 | 100 | 100 | 100 | 100 | 100 | 85 |
| Rice | 65 | 50 | 25 | 0 | 0 | 0 | 75 | 65 | 35 | 20 | 0 | 0 |
| Sorghum | 100 | 100 | 100 | 95 | 85 | 70 | 100 | 100 | 90 | 75 | 65 | 40 |
| Soybean | 100 | 100 | 100 | 100 | 100 | 75 | 100 | 100 | 100 | 100 | 95 | 80 |
| Sugar beet | 100 | 100 | 100 | 100 | 100 | 80 | 100 | 100 | 100 | 100 | 100 | 80 |
| Tomato | 100 | 95 | 65 | 45 | 30 | 20 | 95 | 70 | 40 | 25 | 0 | 0 |

TABLE E-continued

| | Cmpd 1 | | | | | | Cmpd 2 | | | | | |
|---|---|---|---|---|---|---|---|---|---|---|---|---|
| RATE (g/ha) | 125 | 64 | 32 | 16 | 8 | 4 | 125 | 64 | 32 | 16 | 8 | 4 |
| Wheat, Spring | 60 | 40 | 30 | 0 | 0 | 0 | 80 | 65 | 45 | 30 | 0 | 0 |

TEST F

This test illustrates the utility of Compound 1 for weed control in transplanted rice. Note in particular the activity on barnyardgrass and bulrush with transplanted rice tolerance.

Plastic pots were partially filled with silt loam soil. The soil was then saturated with water. Sprouted tubers of arrowhead (*Sagittaria* spp.), barnyardgrass (*Echinochloa crus-galli*) seeds, rough-seeded bulrush (*Scirpus mucronatus*) seedlings at the two to four leaf stage, and japonica rice (*Oryza sativa*) seedlings at the 2.0 to 2.5 leaf stage were planted into this soil. A few days after planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for 21 days, after which all species were compared to contols and visually evaluated. The ratings, summarized in Table F, are based on a scale of 0 to 100 where 0 is no effect and 100 is complete control.

TABLE F

| | Cmpd 1 | | | | |
|---|---|---|---|---|---|
| RATE (g/ha) | 300 | 100 | 30 | 10 | 3 |
| Arrowhead | 90 | 80 | 70 | 0 | 0 |
| Barnyardgrass | 100 | 100 | 100 | 40 | 0 |
| Bulrush | 95 | 95 | 95 | 95 | 90 |
| Rice (Japonica) | 40 | 30 | 20 | 0 | 0 |

What is claimed is:

1. Compounds of the formula

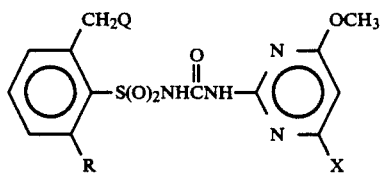

wherein

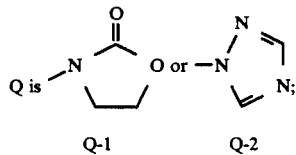

R is Cl, Br, CH$_3$ or SCH$_3$; and
X is CH$_3$, CH$_2$CH$_3$, OCH$_3$ or OCHF$_2$;
and their agriculturally suitable salts.

2. Compounds of claim 1 wherein R is F, Cl, Br or CH$_3$.
3. Compounds of claim 2 wherein R is Cl.
4. Compounds of claim 3 wherein X is CH$_3$ or OCH$_3$.
5. Compounds of claim 1 wherein Q is Q-1.
6. The compounds of claim 5 wherein R is Cl and X is OCH$_3$.
7. The compound of claim 5 wherein R is Cl and X is CH$_3$.
8. Compounds of claim 1 wherein Q is Q-2.
9. The compound of claim 8 wherein R is Cl and X is OCH$_3$.
10. A composition suitable for controlling the growth of undesired vegetation which comprises an effective amount of a compound of claim 1 and at least one of the following: surfactant, solid inert diluent or liquid inert diluent.
11. A composition suitable for controlling the growth of undesired vegetation which comprises an effective amount of a compound of claim 2 and at least one of the following: surfactant; solid inert diluent or liquid inert diluent.
12. A composition suitable for controlling the growth of undesired vegetation which comprises an effective amount of a compound of claim 3 and at least one of the following: surfactant, solid inert diluent or liquid inert diluent.
13. A composition suitable for controlling the growth of undesired vegetation which comprises an effective amount of a compound of claim 4 and at least one of the following: surfactant, solid inert diluent or liquid inert diluent.
14. A composition suitable for controlling the growth of undesired vegetation which comprises an effective amount of a compound of claim 5 and at least one of the following: surfactant, solid inert diluent or liquid inert diluent.
15. A composition suitable for controlling the growth of undesired vegetation which comprises an effective amount of a compound of claim 6 and at least one of the following: surfactant, solid inert diluent or liquid inert diluent.
16. A composition suitable for controlling the growth of undesired vegetation which comprises an effective amount of a compound of claim 7 and at least one of the following: surfactant, solid inert diluent or liquid inert diluent.
17. A composition suitable for controlling the growth of undesired vegetation which comprises an effective amount of a compound of claim 8 and at least one of the following: surfactant, solid inert diluent or liquid inert diluent.
18. A composition suitable for controlling the growth of undesired vegetation which comprises an effective amount of a compound of claim 9 and at least one of the following: surfactant, solid inert diluent or liquid inert diluent.
19. A method for controlling the growth of undesired vegetation which comprises applying to a crop of paddy rice an effective amount of a compound of claim 1.
20. A method for controlling the growth of undesired vegetation which comprises applying to a crop of paddy rice an effective amount of a compound of claim 2.
21. A method for controlling the growth of undesired vegetation which comprises applying to a crop of paddy rice an effective amount of a compound of claim 3.

22. A method for controlling the growth of undesired vegetation which comprises applying to a crop of paddy rice an effective amount of a compound of claim 4.

23. A method for controlling the growth of undesired vegetation which comprises applying to a crop of paddy rice an effective amount of a compound of claim 5.

24. A method for controlling the growth of undesired vegetation which comprises applying to a crop of paddy rice an effective amount of a compound of claim 6.

25. A method for controlling the growth of undesired vegetation which comprises applying to a crop of paddy rice an effective amount of a compound of claim 7.

26. A method for controlling the growth of undesired vegetation which comprises applying to a crop of paddy rice an effective amount of a compound of claim 8.

27. A method for controlling the growth of undesired vegetation which comprises applying to a crop of paddy rice an effective amount of a compound of claim 9.

* * * * *

UNITED STATES PATENT AND TRADEMARK OFFICE
CERTIFICATE OF CORRECTION

PATENT NO.   : 4,981,506
DATED        : January 1, 1991
INVENTOR(S)  : Gene Allen Bozarth et al.

It is certified that error appears in the above-identified patent and that said Letters Patent is hereby corrected as shown below:

Claim 1, delete in the definition of "R " the substituent

-- $CH_3$ --.

Signed and Sealed this

Sixteenth Day of June, 1992

Attest:

DOUGLAS B. COMER

*Attesting Officer*     Acting Commissioner of Patents and Trademarks